US 12,121,695 B2
Oct. 22, 2024

(12) United States Patent
Edwards et al.

(54) INTEGRATED CARTRIDGE ASSEMBLY FOR ADMINISTRATION OF DRUGS

(71) Applicant: MEDPHLOW, LLC, Richmond, VA (US)

(72) Inventors: Eric S. Edwards, Moseley, VA (US); David Johnston, Moseley, VA (US); John McCurley, Powhatan, VA (US); Cristian De La Cotera, Minneapolis, MN (US); Siraaj Dhru, Minneapolis, MN (US); Dallas Erdahl, Minneapolis, MN (US); Dan Johnson, Minneapolis, MN (US); Greg Johnson, Minneapolis, MN (US); Victor Stivala, Bethlehem, PA (US); Brian James, Newton, MA (US); Andrew King, King of Prussia, PA (US)

(73) Assignee: MEDPHLOW, LLC, Richmond, VA (US)

( * ) Notice: Subject to any disclaimer, the term of this patent is extended or adjusted under 35 U.S.C. 154(b) by 0 days.

(21) Appl. No.: 18/687,152

(22) PCT Filed: Jul. 14, 2023

(86) PCT No.: PCT/US2023/027788
§ 371 (c)(1),
(2) Date: Feb. 27, 2024

(87) PCT Pub. No.: WO2024/019938
PCT Pub. Date: Jan. 25, 2024

(65) Prior Publication Data
US 2024/0269374 A1    Aug. 15, 2024

Related U.S. Application Data

(60) Provisional application No. 63/389,992, filed on Jul. 18, 2022.

(51) Int. Cl.
*A61M 5/14*    (2006.01)
*A61M 5/158*   (2006.01)
*A61M 5/168*   (2006.01)

(52) U.S. Cl.
CPC ........ *A61M 5/1413* (2013.01); *A61M 5/1409* (2013.01); *A61M 5/158* (2013.01);
(Continued)

(58) Field of Classification Search
CPC .. A61M 5/1413; A61M 5/1409; A61M 5/158; A61M 5/16813; A61M 2005/1581;
(Continued)

(56) References Cited

U.S. PATENT DOCUMENTS

| 4,850,972 A | 7/1989 | Schulman et al. |
| 5,207,642 A | 5/1993 | Orkin et al. |

(Continued)

FOREIGN PATENT DOCUMENTS

| EP | 2283885 | 2/2011 |
| WO | WO2010/014654 | 2/2010 |
| WO | WO2024/054565 | 3/2024 |

OTHER PUBLICATIONS

International Search Report and Written Opinion for PCT/US2023/02778, mailed Oct. 20, 2023.
(Continued)

*Primary Examiner* — Theodore J Stigell
(74) *Attorney, Agent, or Firm* — Ambrose, Mills & Lazarow, PLLC

(57) ABSTRACT

An integrated cartridge assembly that is employed with an automated medication administration system in response to the acute medical condition. The cartridge assembly configured to be operatively coupled between a pump assembly and a medical port. The cartridge assembly includes a first cartridge and a second cartridge positioned within a housing.
(Continued)

The first cartridge contains a portion of saline, while the second cartridge contains a portion of a medicament. The cartridge assembly also includes a gate member that maintains a separation distance between a manifold assembly and the first and second cartridges when in a locked position when the cartridge assembly is in the stored state. The cartridge assembly is operatively coupled to the medical port via a tube set that is fixedly coupled to the manifold assembly.

22 Claims, 33 Drawing Sheets

(52) U.S. Cl.
CPC . *A61M 5/16813* (2013.01); *A61M 2005/1581* (2013.01); *A61M 2205/121* (2013.01)

(58) Field of Classification Search
CPC .. A61M 2205/121; A61M 5/343; A61M 5/19; A61M 39/18; A61M 2005/14272
See application file for complete search history.

(56) References Cited

U.S. PATENT DOCUMENTS

| | | | |
|---|---|---|---|
| 5,243,982 | A | 9/1993 | Mostl et al. |
| 5,298,021 | A | 3/1994 | Sherer |
| 5,298,023 | A * | 3/1994 | Haber ............... A61M 5/322 604/211 |
| 7,316,231 | B2 | 1/2008 | Hickle |
| 7,575,567 | B2 | 8/2009 | Simpkins |
| 7,608,060 | B2 | 10/2009 | Gillespie, Jr. et al. |
| 7,815,605 | B2 | 10/2010 | Souter |
| 7,917,208 | B2 | 3/2011 | Yomtov et al. |
| 7,963,945 | B2 | 6/2011 | Miller et al. |
| 8,812,101 | B2 | 8/2014 | Miller et al. |
| 9,398,894 | B2 | 7/2016 | Patrick et al. |
| 9,814,872 | B2 | 11/2017 | Eggert et al. |
| 9,987,410 | B2 * | 6/2018 | Helmore ............... A61M 1/14 |
| 10,071,203 | B2 | 9/2018 | Edwards et al. |
| 10,668,247 | B2 | 6/2020 | Anand et al. |
| 10,675,438 | B2 | 6/2020 | Anand et al. |
| 10,682,067 | B2 | 6/2020 | Tan et al. |
| 10,828,424 | B2 | 11/2020 | Anand et al. |
| 10,926,024 | B2 | 2/2021 | Mackenzie et al. |
| 2007/0088271 | A1 | 4/2007 | Richards |
| 2010/0022987 | A1 | 1/2010 | Bochenko et al. |
| 2010/0198280 | A1 | 8/2010 | Corndorf et al. |
| 2012/0078181 | A1 | 3/2012 | Smith et al. |
| 2013/0296823 | A1 | 11/2013 | Melker et al. |
| 2020/0155401 | A1 | 5/2020 | Wang et al. |
| 2020/0297966 | A1 | 9/2020 | Anand et al. |
| 2021/0030947 | A1 | 2/2021 | Damiano et al. |
| 2021/0052820 | A1 | 2/2021 | Anand et al. |
| 2021/0085859 | A1 | 3/2021 | Oshinski et al. |
| 2021/0128821 | A1 | 5/2021 | Mackenzie et al. |
| 2024/0139406 | A1 | 5/2024 | Mackenzie et al. |

OTHER PUBLICATIONS

Todd B. Brown et al., "Relationship Between Knowledge of Cardiopulmonary Resuscitation Guidelines and Performance", Department of Emergency Medicine, University of Alabama, Birmingham, AL, USA, Resuscitation Elsevier, (2006) vol. 69, pp. 253-261.
Kathy Dittrich, "ACLS update: A new role for medications," Critical Care, www.nursing2007.com, December, Nursing2007, pp. 56cc1-56cc3.
Alexander H. Flannery et al., "Medication Errors in Cardiopulmonary Arrest and Code-Related Situations", AJCC American Journal of Critical Care, Jan. 2016, vol. 25, No. 1, pp. 12-20.
ISMP Institute for Safe Medication Practices, "Two Unsafe Practices: Administration of a Product with a Precipitate and Reuse of a Saline Flush Syringe," Featured Articles, online, <https://www.ismp.org/resources/two-unsafe-practices-administration-product-precipitate-and-reuse-saline-flush-syringe> Apr. 6, 2017, 6 pages.
Phil Jevon, "The Administration of Drugs During Resuscitation," Clinical Practical Procedures, Nursing Times, vol. 103, No. 11, www.nursingtimes.net, Mar. 13, 2007, pp. 26-27.
Luer-Jet™ "Needleless Emergency Syringes," International Medication Systems, Ltd., An Amphastar Pharmaceuticals Company, www.ims-limited.com, Rx Only Apr. 2019, 2 pages.
Tara McCurdie et al., "The Use of Multiple Methods to Explore the Impact of Interruptions on Intravenous (IV) Push Delivery," Proceedings of the Human Factors and Ergonomics Society 58th Annual Meeting—Oct. 2014, pp. 738-742.
Dariush Mozaffarian et al., "Executive Summary: Heart Disease and Stroke Statistics—2015 Update a Report From the American Heart Association", UC San Francisco Previously Published Works, Jan. 27, 2015, pp. 434-441.
Chika Nishiyama et al., "Long-term Retention of Cardiopulmonary Resuscitation Skills After Shortened Chest Compression-only Training and Conventional Training: A Randomized Controlled Trial", Academic Emergency Medicine, Official Journal of the Society for Academic Emergency Medicine, 2013, pp. 47-54.
International Search Report and Written Opinion for PCT/US2023/032183, mailed Apr. 4, 2024.

* cited by examiner

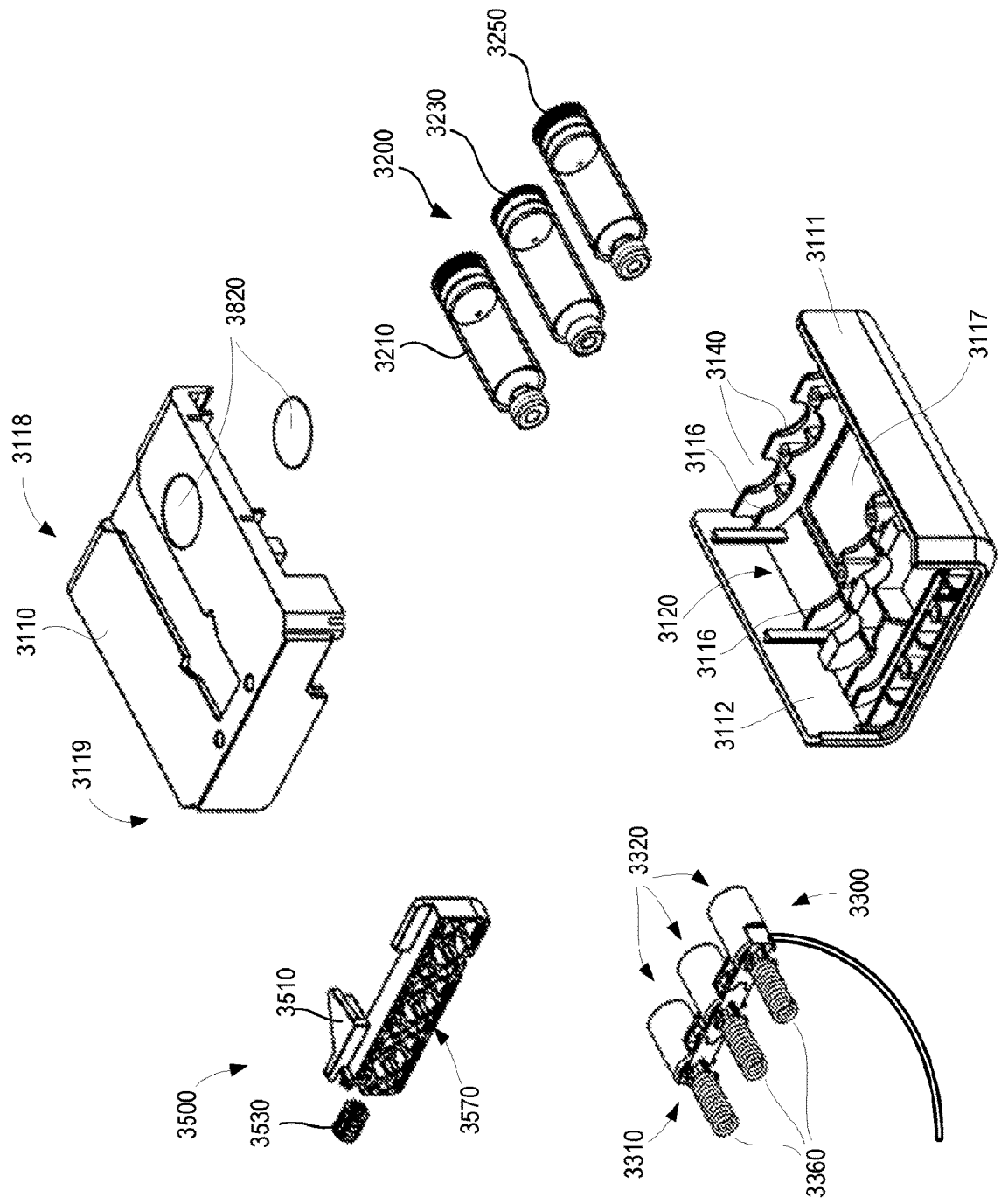

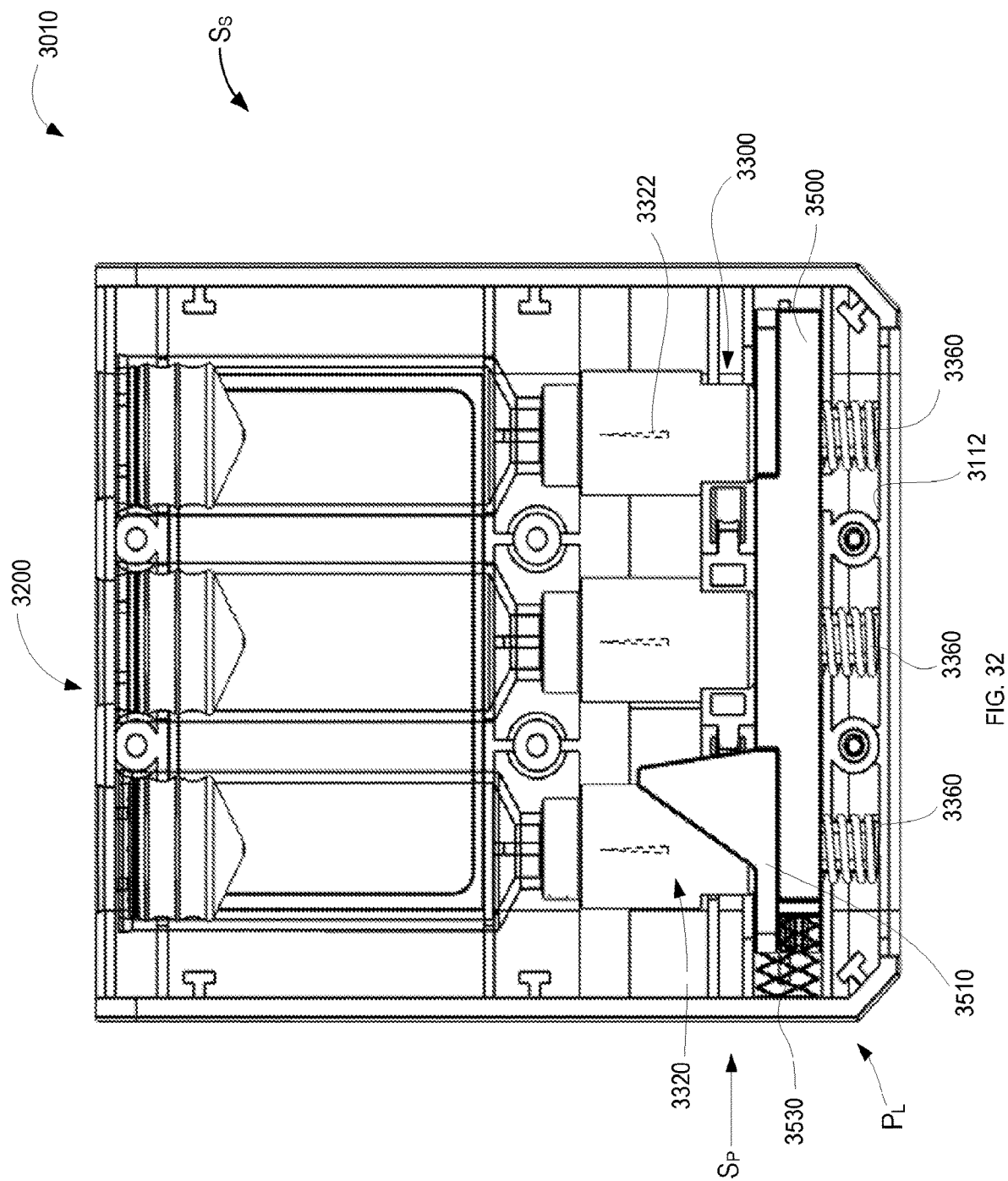

INTEGRATED CARTRIDGE ASSEMBLY FOR ADMINISTRATION OF DRUGS

CROSS-REFERENCE TO RELATED APPLICATIONS

This application is a U.S. national stage filing under 35 U.S.C. § 371 of International Application No. PCT/US2023/027788, entitled "Integrated Cartridge Assembly for Administration of Drugs." filed Jul. 14, 2023, which claims priority to and the filing date benefit of U.S. Provisional Patent Application No. 63/389,992, filed Jul. 18, 2022, and entitled "Integrated Cartridge Assembly for Administration of Drugs," the disclosures of which is are incorporated herein by reference in its entirety.

BACKGROUND

The embodiments described herein relate to systems, apparatuses, applications, methodologies and other tools to administer medications and other treatments to patients experiencing an acute medical condition (e.g., cardiac arrest and trauma-induced hemorrhaging) as well as other prolonged acute and critical care management situations (e.g., trauma-related pain and burn relief, sedation, and ani-anxiety). In particular this disclosure relates to an integrated cartridge assembly that is employed with an automated medication administration system in response to the acute medical condition.

Heart disease is the leading cause of death worldwide with 17.3 million deaths each year. That number is expected to rise further by 2030 to 23.6 million. Conditions such as hypertension, hyperlipidemia, electrolyte imbalances, and trauma may lead to cardiac arrest where the patient's heart cannot provide adequate blood supply to vital organs, leading to severe injury or death. Cardiac arrest also compromises blood flow to the heart itself, leading to ischemia. Providing proper medical intervention soon after the onset of cardiac arrest is vital. In the United States, only about 10% of people who sustain a cardiac arrest survive. The survival rate triples when an arrest is witnessed by a bystander who can provide immediate assistance by administering cardiopulmonary resuscitation CPR and/or by summoning aid.

A "code" is a medical term used to describe a situation where a patient requires resuscitative efforts by a team of medical professionals, usually because the patient is experiencing cardiopulmonary arrest. Cardiopulmonary arrest may be due to various underlying causes resulting in an abnormal heartbeat or the absence of a heartbeat. Generally, treatments provided during a code focus on resuscitative efforts to restore a normal or near normal heartbeat to maintain blood flow throughout the body. Because vital organs and the central nervous system can be injured by interruption of blood flow for even short amounts of time, medical treatment during a code needs to be performed quickly. Often decisions to administer treatment during a code are complex and depend on the patient's medical condition, which may change from moment to moment.

Common interventions performed during a code include chest compressions (to compensate for a patient's heart not beating normally on its own), rescue breathing (to increase the level of oxygen in circulating blood), electrical shocks (to stimulate a patient's heart to beat normally), and delivery of various medications (to stimulate the heart or change the rhythm in which the heart is beating). Non-medical rescuers may learn skills focused on the first two of these interventions as part of Basic Life Support (BLS). Additionally, people trained in BLS may learn how to use an Automated External Defibrillator (AED), a device that interprets a patient's heart rhythm and potentially delivers an electrical shock based on that interpretation. BLS and use of an AED are based on established protocols. For example, BLS includes determining the patient's condition and administering chest compressions, rescue breathing, and/or electrical stimulation with an AED.

Medical professionals (e.g., emergency responders, nurses, pharmacists, physicians, nurse practitioners, physician assistants, etc.) may learn a more advanced form of intervention that, like BLS, is also largely protocol-based. For adult patients, this set of protocols or algorithms is known as Advanced Cardiac Life Support (ACLS). For children, this is known as Pediatric Advanced Life Support (PALS). ACLS and PALS focus on additional medication delivery and rescuer-selected electrical intervention based on a rescuer's interpretation of various cardiac rhythms. PALS is similar to ACLS but it utilizes weight-based medication dosages.

Code situations are often chaotic, with life-or-death decisions being made by a code leader and communicated to other professionals verbally and under time pressure. These circumstances can lead to errors in treatment. For example, the code leader's instructions regarding the medication, dosage, or route of administration may be misunderstood by team members, e.g., instructions to administer 1 mg of 1:1,000 concentration epinephrine instead of the appropriate 1:10,000 concentration. In addition, there may be errors in how medications are prepared or labeled, or which medication is actually administered because packaging or labeling of different medications look similar.

In accordance with the ACLS and PALS algorithms, specific doses of particular medications must be given at prescribed time intervals based upon the characteristics of the patient and patient's response to interventions. For example, under the ACLS protocol, epinephrine is administered in 1 mg doses every three to five minutes. Similarly, a first 300 mg dose of amiodarone is administered with a second 150 mg dose following, after a prescribed interval. Accordingly, it is desirable that the full prescribed dosage of the correct medication be administered to the patient at the prescribed intervals and that the full prescribed dose reach the patient, even under the chaos of the code situation. However, the time-constrained and rapidly evolving nature of a code situation may present challenges related to rapidly locating appropriate medications, manual dose calculations, therapeutic preparations, complete dose delivery, manual administration into an access port, proper adherence to a protocol sequence.

The time stress of a code situation also makes it difficult to create a record of what treatments were administered, at what time, and in the context of the patient's condition. In the case of cardiac arrest, the patient's condition may change rapidly. Decisions by the code leader and other code team members are made in response to the patient's condition and there may not be time to record what was done. Poor recordkeeping during the code may make it difficult for team members and other professionals to learn how to improve or to assess whether proper treatment was given. Additionally, poor recordkeeping can negatively impact the hand off of the patient between health care providers as such a hand off includes information about recently administered drugs, dosages, and timings.

Accordingly, there is a need for an integrated cartridge assembly that is employed with an automated medication administration system to deliver drugs in response to the acute medical condition.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, the present disclosure is directed to a cartridge assembly configured to be operatively coupled between a pump assembly and a medical port. The cartridge assembly includes a housing having a wall. An inner face of the wall defines an internal volume. An outer face of the wall has a coupling member positioned to engage a coupling interface of the pump assembly. A first cartridge is positioned within the internal volume. The first cartridge includes a first container body, a first frangible seal coupled to the first container body, and a first elastomeric member disposed within the first container body to retain a portion of saline within the first cartridge. A second cartridge is also positioned within the internal volume. The second cartridge similarly includes a second container body, a second frangible seal coupled to the second container body, and a second elastomeric member disposed within the second container body. The second elastomeric member retains a portion of a medicament within the second cartridge. The cartridge assembly also includes a manifold assembly positioned within the internal volume. The manifold assembly includes a manifold housing defining a receiving volume, a set of puncturers in fluid communication with the receiving volume and oriented to puncture the first frangible seal and the second frangible seal, and a plurality of one-way valves disposed between the set of puncturers and the receiving volume. A tube set is fixedly coupled to the manifold assembly in fluid communication with the receiving volume. The tube set is also configured to be coupled to the medical port. Additionally, the cartridge assembly includes a gate member positioned within the internal volume. The gate member has an actuation portion at a position between the outer face and the coupling member. The gate member maintains a separation distance between the puncturers and the first frangible seal and the second frangible seal when in a locked position when the cartridge assembly is in a stored state.

BRIEF DESCRIPTION OF THE DRAWINGS

FIG. 30 is an exploded perspective view of the cartridge assembly of FIG. 29.

FIG. 32 is a top view of the cartridge assembly of FIG. 29 with a portion of the housing removed.

DETAILED DESCRIPTION

Figure 1:
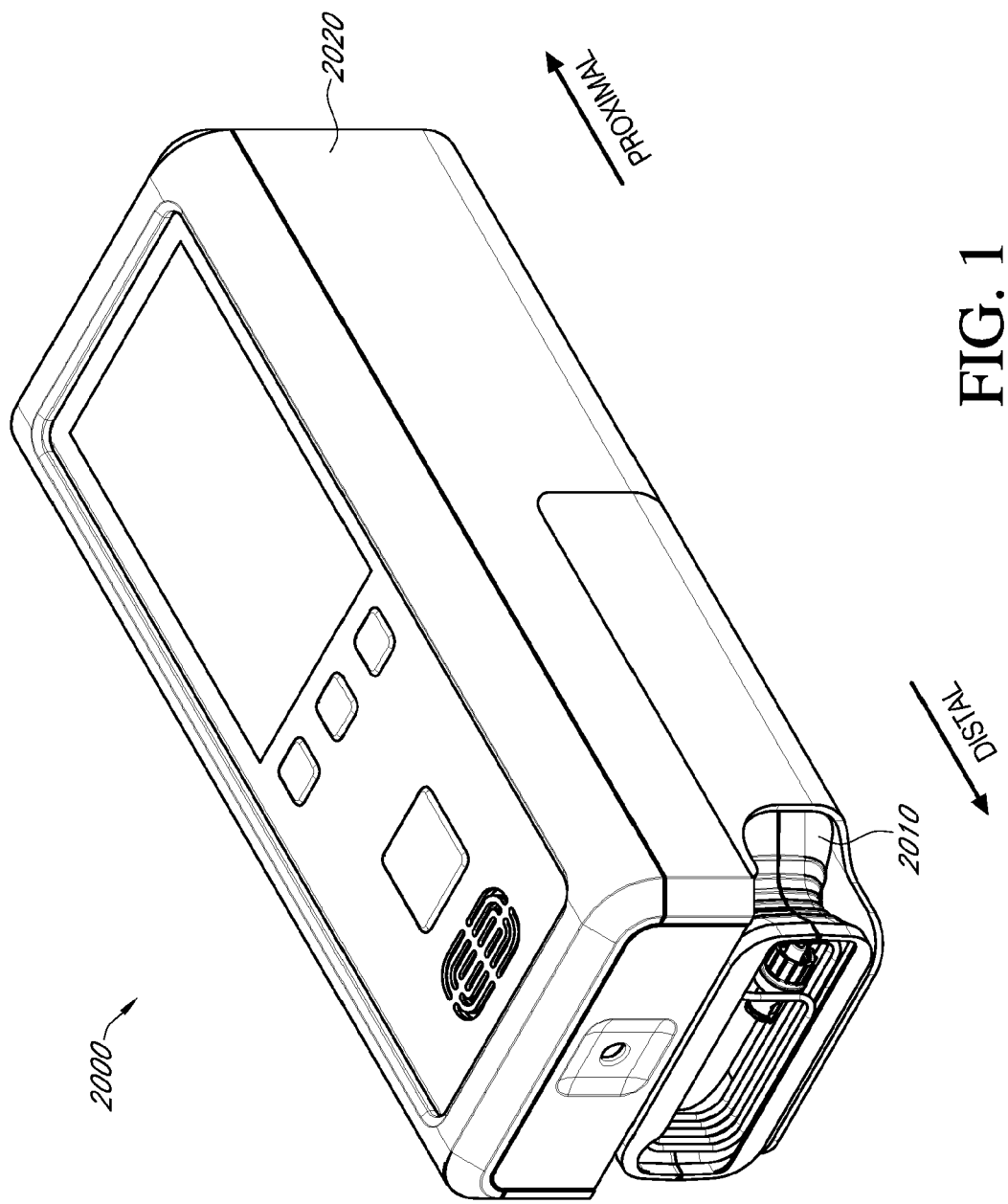
FIG. 1 is a perspective view of an acute medical condition response system in an assembled configuration according to an embodiment.
Figure 2:
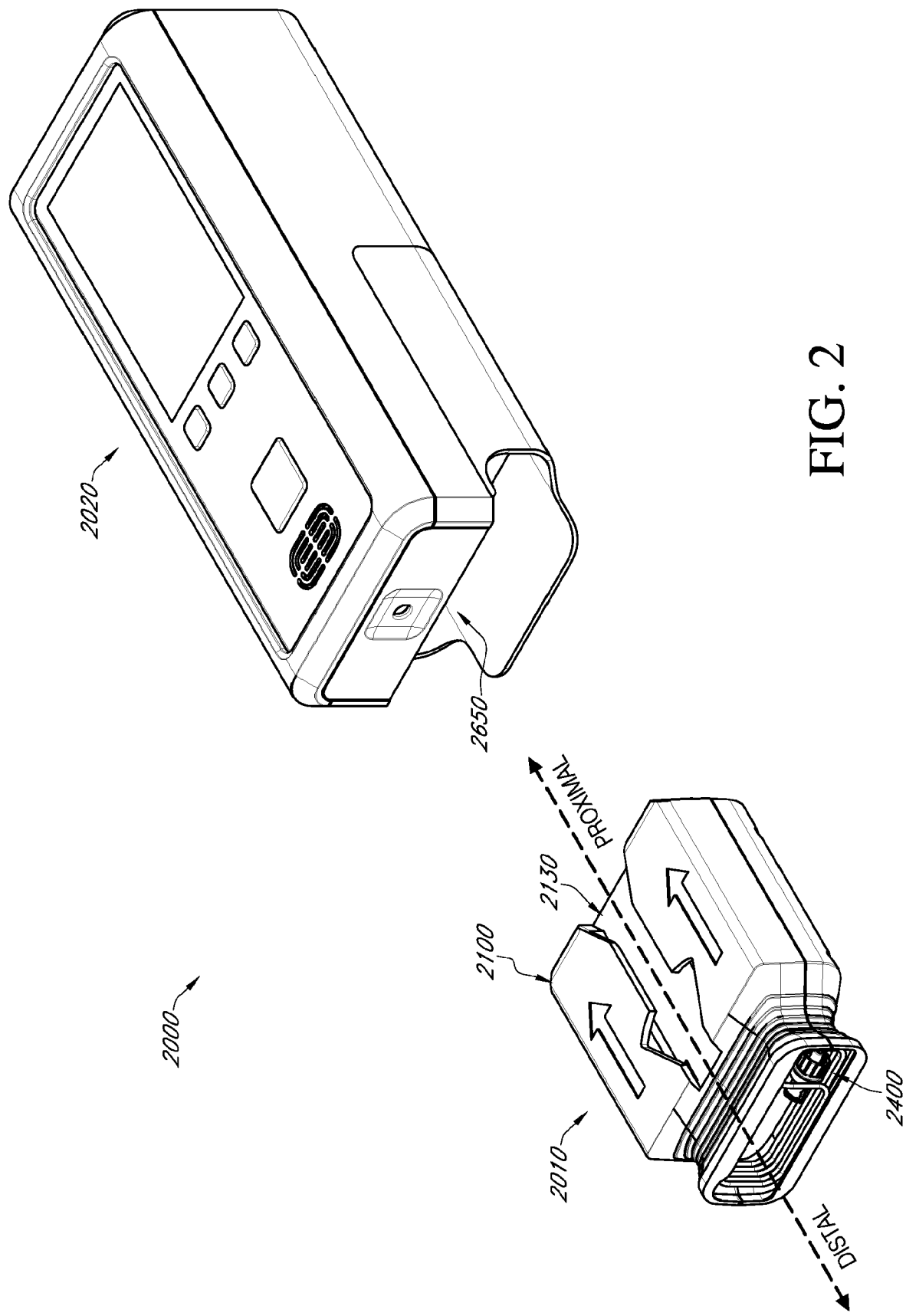
FIG. 2 is a perspective view of the system of FIG. 1 with the cartridge assembly separated from the pump assembly.
Figure 3:
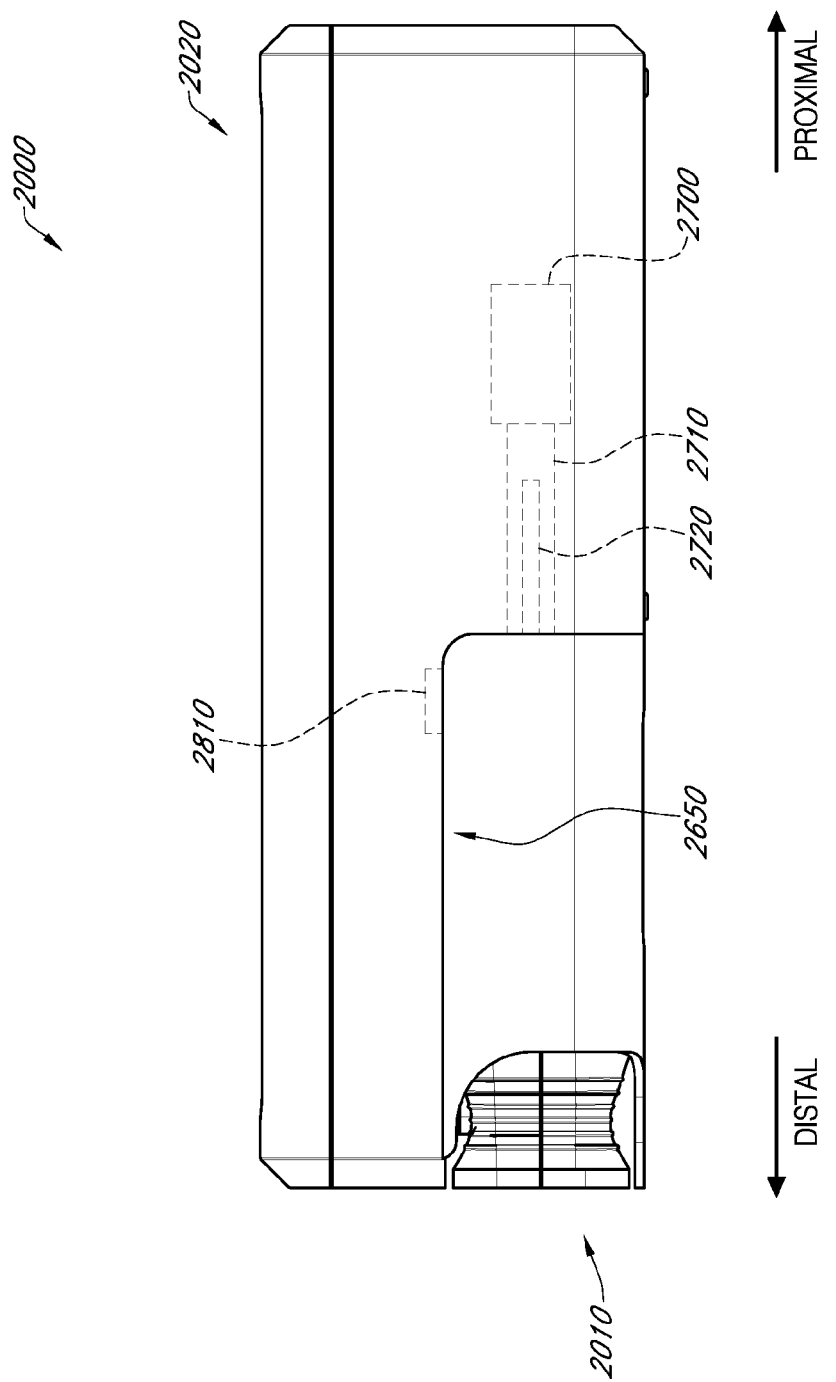
FIG. 3 is a side view of the system of FIG. 1.

Generally, the present disclosure is directed to systems and methods for administering medication in response to an acute medical condition. As disclosed herein, the acute medical condition response system (also referred to as an Automated Medication Administration System (AMAS)) is a drug-device combination product designed to automatically deliver at least one drug followed by a portion of saline or another drug in response to specified acute medical conditions. For example, the system can be configured to automatically deliver epinephrine and/or amiodarone during cardiopulmonary resuscitation (CPR) of adults and pediatric victims of cardiac arrest. The system will deliver the drugs according to the dosing and timing recommended in established treatment protocols (e.g., the American Heart Association's algorithms for treatment of adult and pediatric cardiac arrest). The system is intended to be used in both out-of-hospital and in-hospital settings, to enable a shorter time to administer of the drugs, ensure accurate dosing, keep automated records of the dose, and eliminate the human delay and medication error that may result from drawing up from a vial, and/or use of multiple syringes.

The system can be of particular benefit in pediatric cases where drugs are dosed based on the patient's weight. For example, the target dose for pediatric use can be weight-based at 5 mg/kg, with patients weighing between 3 kg and 30 kg, inclusive. In such a case, the target volume of an amiodarone hydrochloride injection to be delivered over this pediatric weight range ranges from 0.3 mL to 3 mL, based on the weight-based pediatric 5 mg/kg dose. As such, the system described herein is configured to facilitate the accurate dispensing of relatively small volumes (e.g., 0.3 mL). The system also employs an on-board saline flush to ensure that the entirety of the dispensed volume is delivered to the patient.

As described herein, the system includes a cartridge assembly that is coupled to a pump assembly and is also coupled to a medical port (e.g., an intravenous (IV) catheter, an IV cannula, a central venous access device, an intraosseous (IO) access device, an implanted port, a peripherally inserted central catheter (a PICC line), or other medical implement for facilitating access to the circulatory system of the patient). The cartridge assembly contains at least two color-coded cartridges. One cartridge contains a medicament, such as epinephrine or amiodarone hydrochloride, while the other cartridge contains a sodium chloride (saline) solution. Each of the cartridges are sealed with a frangible seal when the cartridge assembly is in a stored state. When actuated, the frangible seals are punctured by a number of puncturers (e.g., needles) of a manifold assembly within the cartridge assembly. This actuation places the cartridges in fluid communication with the medical port (e.g., a vascular access device) via a tube set that has a specified volume. The pump assembly can then deliver a dose of the medicament in accordance with the protocol being implemented. This is followed by delivering a portion of the saline from the cartridge assembly. By following the medicament with the portion of saline, the system ensures that the entirety of the prescribed dose is flushed from the tube set and delivered accurately to the patient. This process can be repeated in accordance with the protocol.

As further described herein, the cartridge assembly is a sealed system in which the cartridges are not accessible to the user. Thus, the cartridges are prefilled with multiple doses at the desired concentration and formulation of medicament and are ready for automated delivery without the need for the user to prepare a delivery syringe with a desired type and amount of medicament. A viewing port in the housing allows intended users to visually inspect the cartridges (e.g., glass cartridges) within the cartridge assembly. In some embodiments, the cartridge assembly contains three individual glass cartridges that contain epinephrine, amiodarone HCl, and sodium chloride, respectively. The cartridges utilize colored aluminum crimp seals for each cartridge to ensure differentiation and inspection. The cartridge assembly also includes a sensor interface (e.g., an RFID tag) that is readable by a sensor of the pump assembly and indicates whether the cartridge is configured for an adult patient or a pediatric patient. The sensor interface can also indicate other information about the cartridge, such as an expiration date, a manufacture date, lot information, a storage compliance indication, a recall status, and/or a prior actuation of the cartridge. For example, the sensor interface may indicate that a cartridge has been previously used and the system may generate an error.

The utilization of the acute medical condition response system reduces the cognitive load of the care providers when responding to an acute medical condition by automating aspects of medication selection, dosage delivery, and adherence to a dosage schedule. This, in turn, facilitates the focus of the care providers on treating reversible causes. For example, each cartridge assembly contains sufficient dosages of the prescribed drug to comply with the dosage schedule of the implemented protocol and the pump assembly facilitates the delivery of the prescribed dose. Additionally, the utilization of the tube set having a prescribed volume in conjunction with the bolus of saline from the saline cartridge ensures the accuracy of the prescribed dose that is delivered to the patient. This may be especially beneficial to ensure accuracy for the relatively small volumes corresponding to pediatric patients.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the terms "proximal" and "distal" refer to direction closer to and away from, respectively, an operator of the system. Thus, for example, the end of the cartridge assembly closest to or contacting the patient's body would be the distal end of the cartridge assembly, while the end opposite the distal end (i.e., the end closer to the operator) would be the proximal end of the system.

Further, specific words chosen to describe one or more embodiments and optional elements or features are not intended to limit the invention. For example, spatially relative terms-such as "beneath", "below", "lower", "above", "upper", "proximal", "distal", and the like may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Figure 6A:
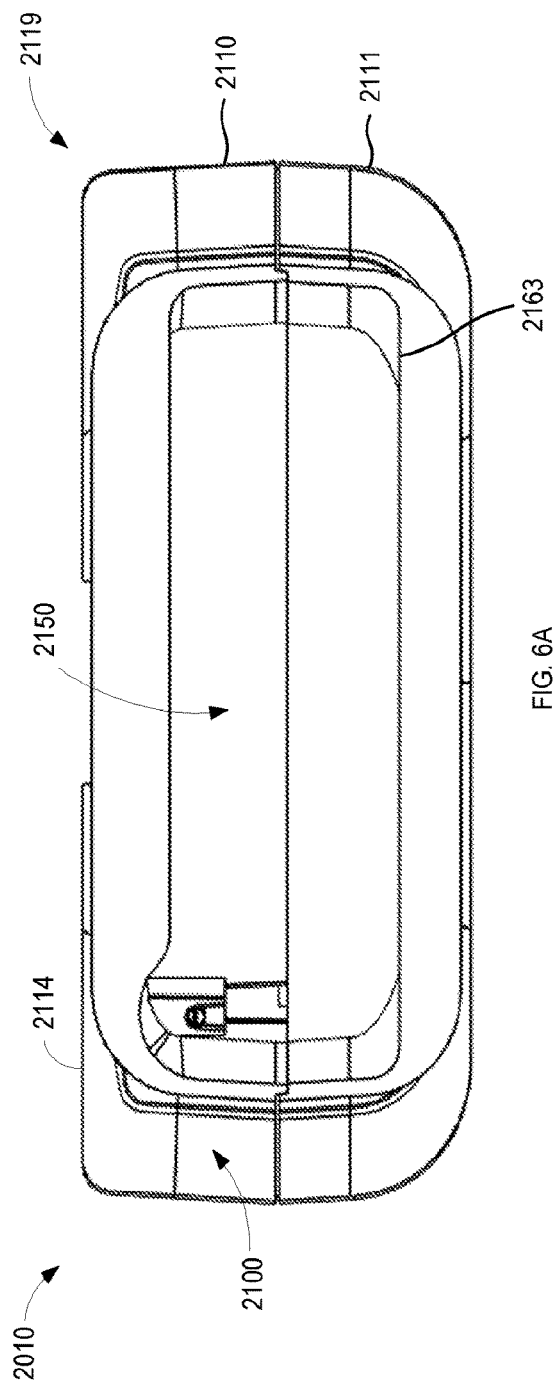
FIG. 6A is a front view of the cartridge assembly of FIG. 2.
Figure 7:
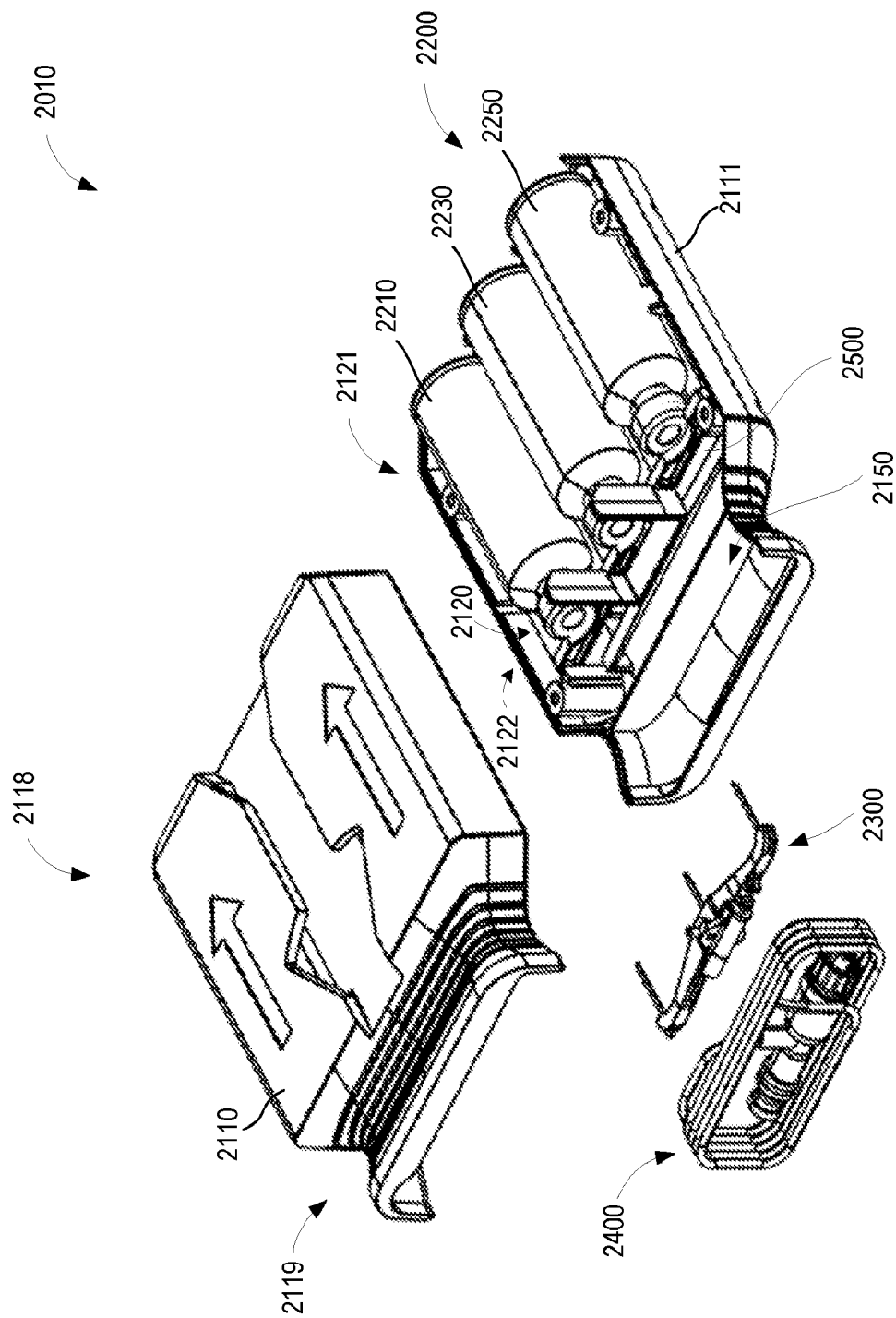
FIG. 7 is an exploded perspective view of the cartridge assembly of FIG. 2.
Figure 8:
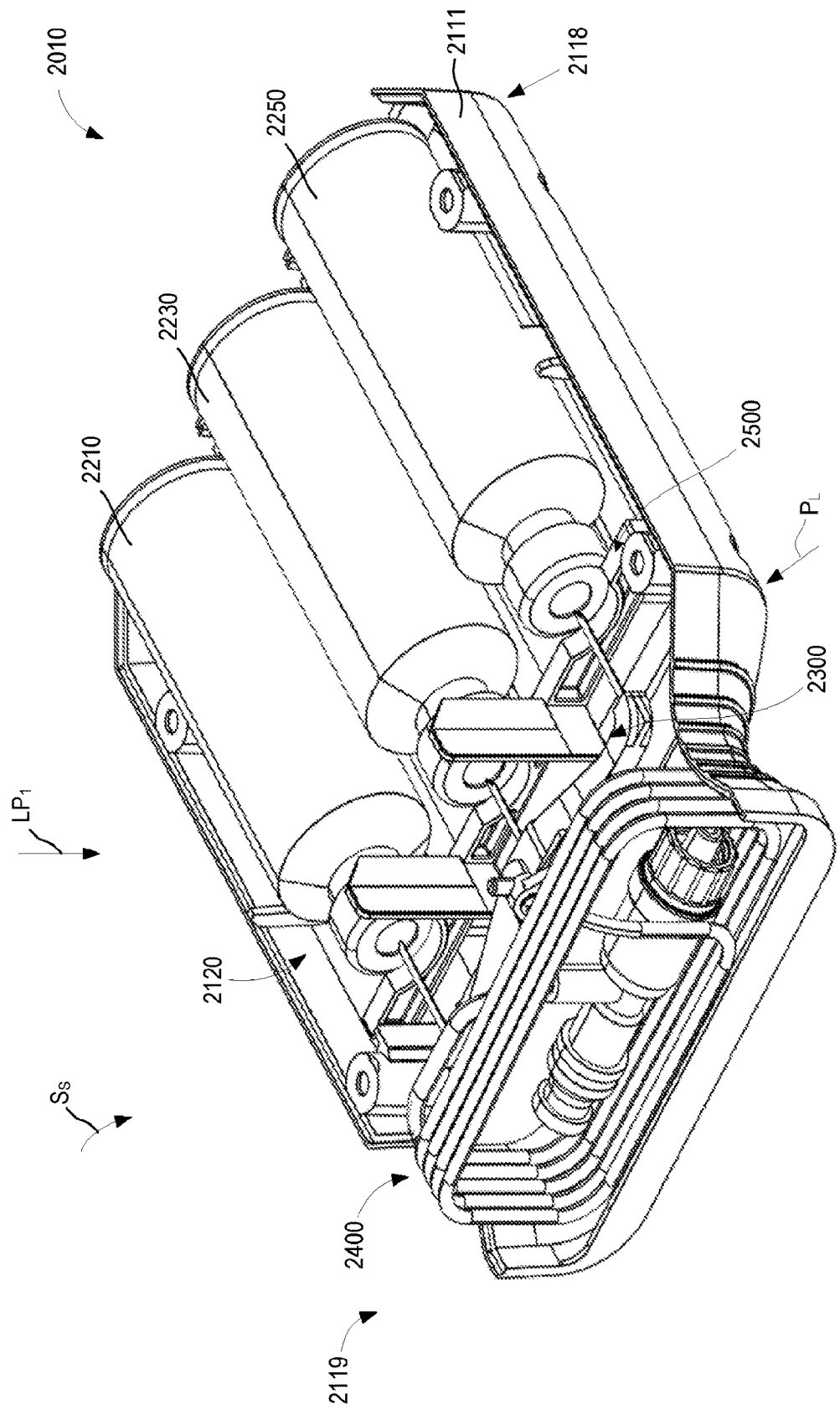
FIG. 8 is a perspective view of the cartridge assembly of FIG. 2 in a storage configuration (i.e., prior to being coupled to the pump), with a portion of the cartridge housing removed.
Figure 9:
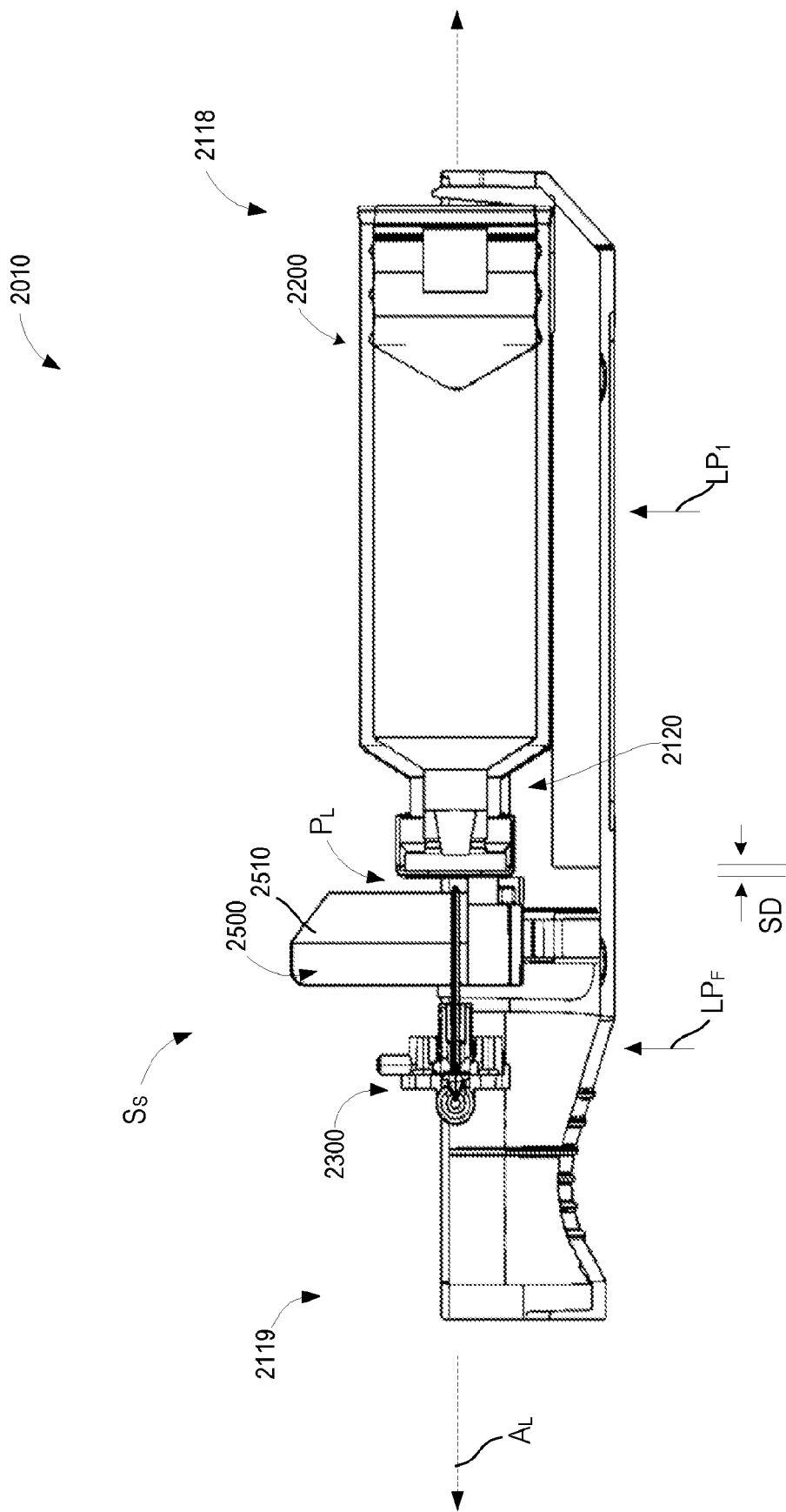
FIG. 9 is a side view of the cartridge assembly in the storage configuration as depicted in FIG. 8.
Figure 10:
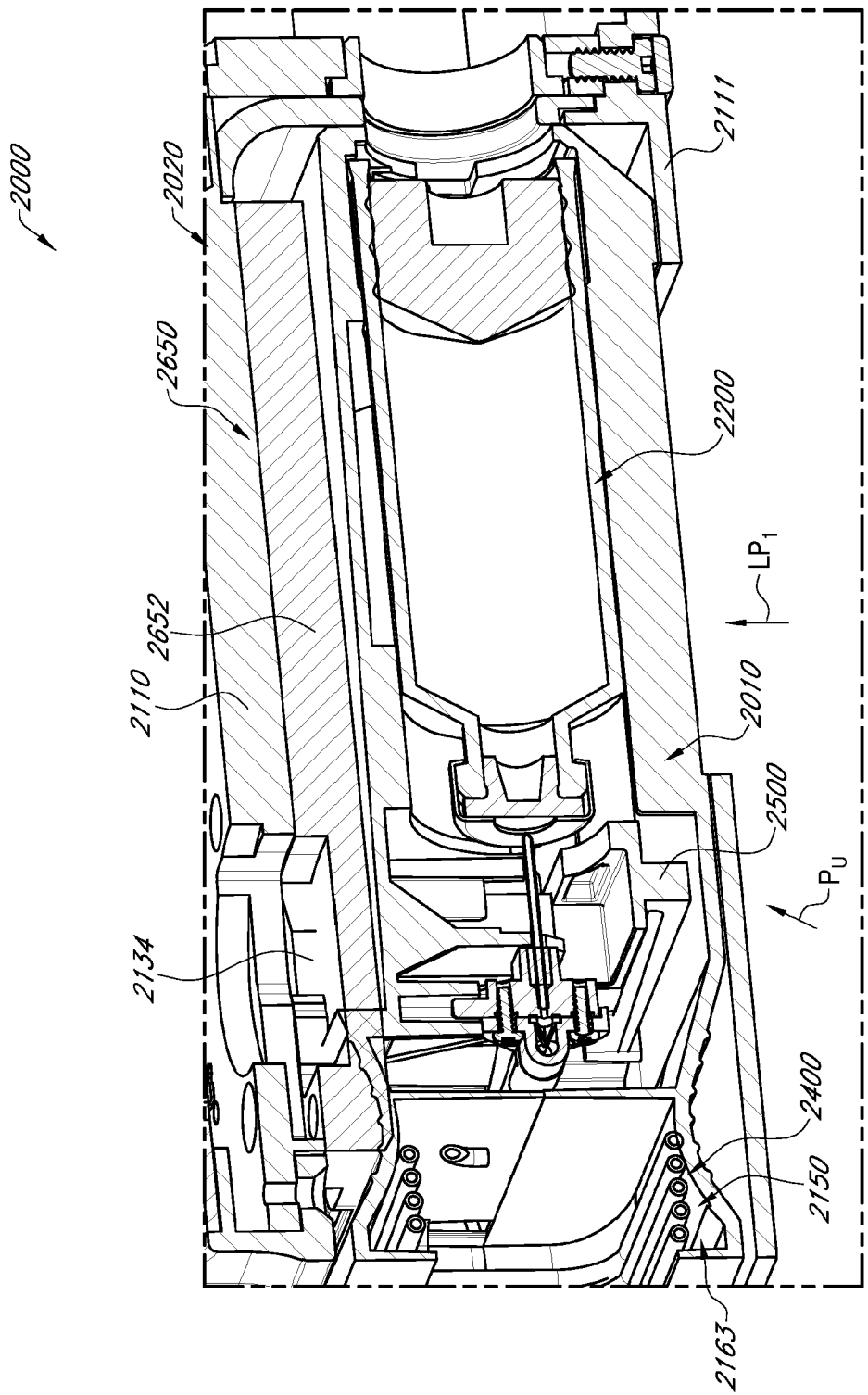
FIG. 10 is a cross-sectional view of a portion of the system of FIG. 1, showing the cartridge assembly in a first (i.e., loaded) configuration (coupled to the pump, but prior to actuation).
Figure 11:
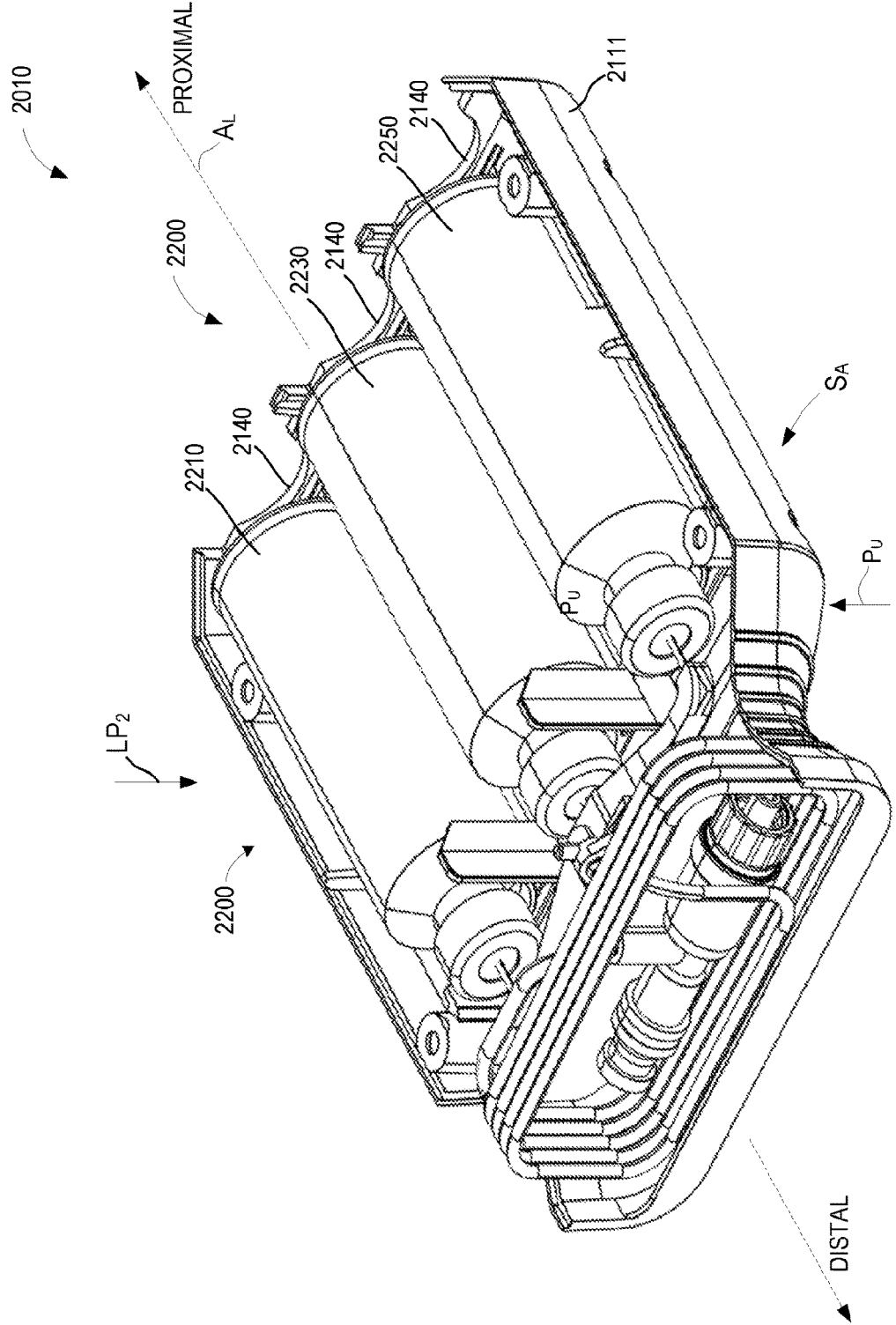
FIG. 11 is a perspective view of the cartridge assembly of FIG. 2 in a second configuration (i.e., an actuated configuration, after the cartridges are in fluid communication with the manifold assembly), with a portion of the cartridge housing removed.
Figure 12:
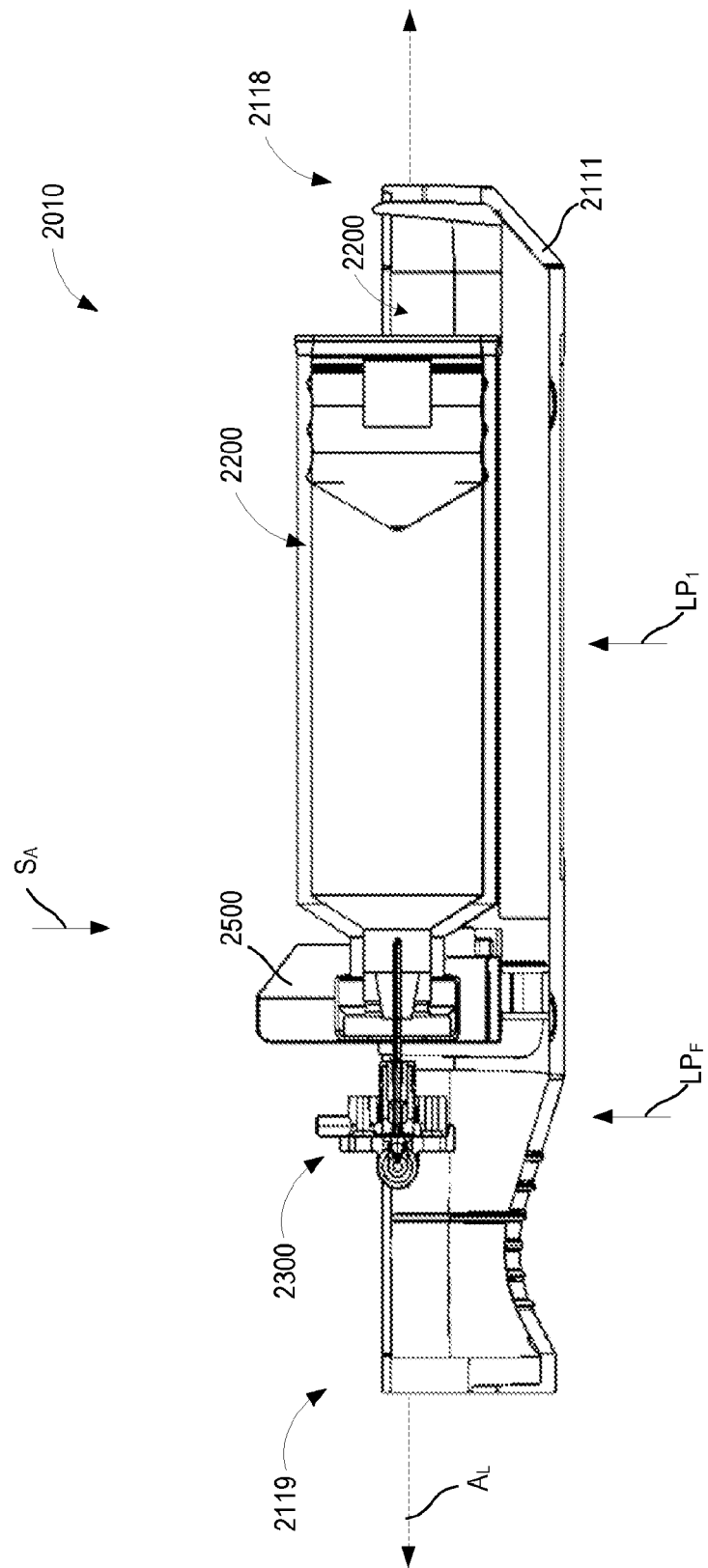
FIG. 12 is a side view of the cartridge assembly in the second configuration as depicted in FIG. 11.

FIGS. 1-25B depict various aspects of an acute medical condition response system (system) (also referred to as an Automated Medication Administration System (AMAS) or "system") 2000. As described herein, the system 2000 is configured to automate certain aspects of a response to an acute medical condition, such as cardiac arrest. Accordingly, the system 2000 utilizes a sealed cartridge assembly 2010 containing more than one dose of a drug (e.g., epinephrine, amiodarone hydrochloride, or other desired medicament) and more than one dose of a separate saline solution. The cartridge assembly 2010 is configured to be operably coupled between a pump assembly 2020 and a medical port (not shown) that is inserted into or attached to a patient. In this manner, the system 2000 can be used with a conventional medical port. The cartridge assembly 2010 includes a housing 2100 having a wall that defines an internal volume 2120 (see FIG. 8) and includes a coupling member 2130. The coupling member 2130 is positioned to engage a coupling interface 2650 of the pump assembly 2020. A set of cartridges 2200 is positioned within the internal volume 2120. In this embodiment, the cartridge assembly 2010 includes a first cartridge 2210 that contains a portion of saline 2218, a second cartridge 2230 that contains a first medicament 2238, and a third cartridge 2250 that contains a second medicament 2258. A manifold assembly 2300 is also positioned within the internal volume 2120. As depicted in FIGS. 11-12, the manifold assembly 2300 includes a set of puncturers 2320 oriented to fluidically couple each of the cartridges 2200 to a tube set 2400 when the cartridge assembly 2010 is actuated. However, a gate member 2500 is also positioned within the internal volume 2120 to maintain a separation distance SD (see FIG. 9) between the set of puncturers 2320 and the set of cartridges 2200 when the cartridge assembly 2010 is in either a storage configuration as depicted in FIGS. 8-9 or in a first (or loaded) configuration as depicted in FIG. 10. In this manner, the gate member 2500 functions as a safety to prevent the undesired or premature actuation of the cartridge assembly 2010.

In some embodiments, the cartridge assembly 2010 can be stored in a sterile package (not shown) until an acute medical condition is encountered. The sterile package can include a peel-away seal or a perforation for opening. In some embodiments, the sterile package can be constructed from a porous polymer that is formulated to allow a sterilant gas or substance to pass therethrough, while substantially preventing pathogens or microbes from passing therethrough. In this manner, the cartridge assembly 2010 can be sterilized after manufacture. In some embodiments, the sterile package can be constructed from any one of polyethylene, high-density polyethylene (i.e., Tyvek®), polypropylene, polytetrafluoroethylene, or thermoplastic polyurethane. The sterile package can be used with any suitable sterilization technique or medium, including ethylene oxide, gamma radiation, e-beam radiation, ultraviolet radiation, steam, plasma, or hydrogen peroxide. In some embodiments, the peel-away seal or the perforated region can include tamper indicating features (e.g., a feature that changes color if opened, a non-resealable feature, or the like). Markings may be applied to the packaging to indicate whether the cartridge assembly 2010 is an adult cartridge assembly or a pediatric cartridge assembly. The markings may also provide additional information related to the manufacture and/or usage of the cartridge assembly 2010. In some embodiments, a desiccant or other additives can be included in the packaging.

Figure 13:
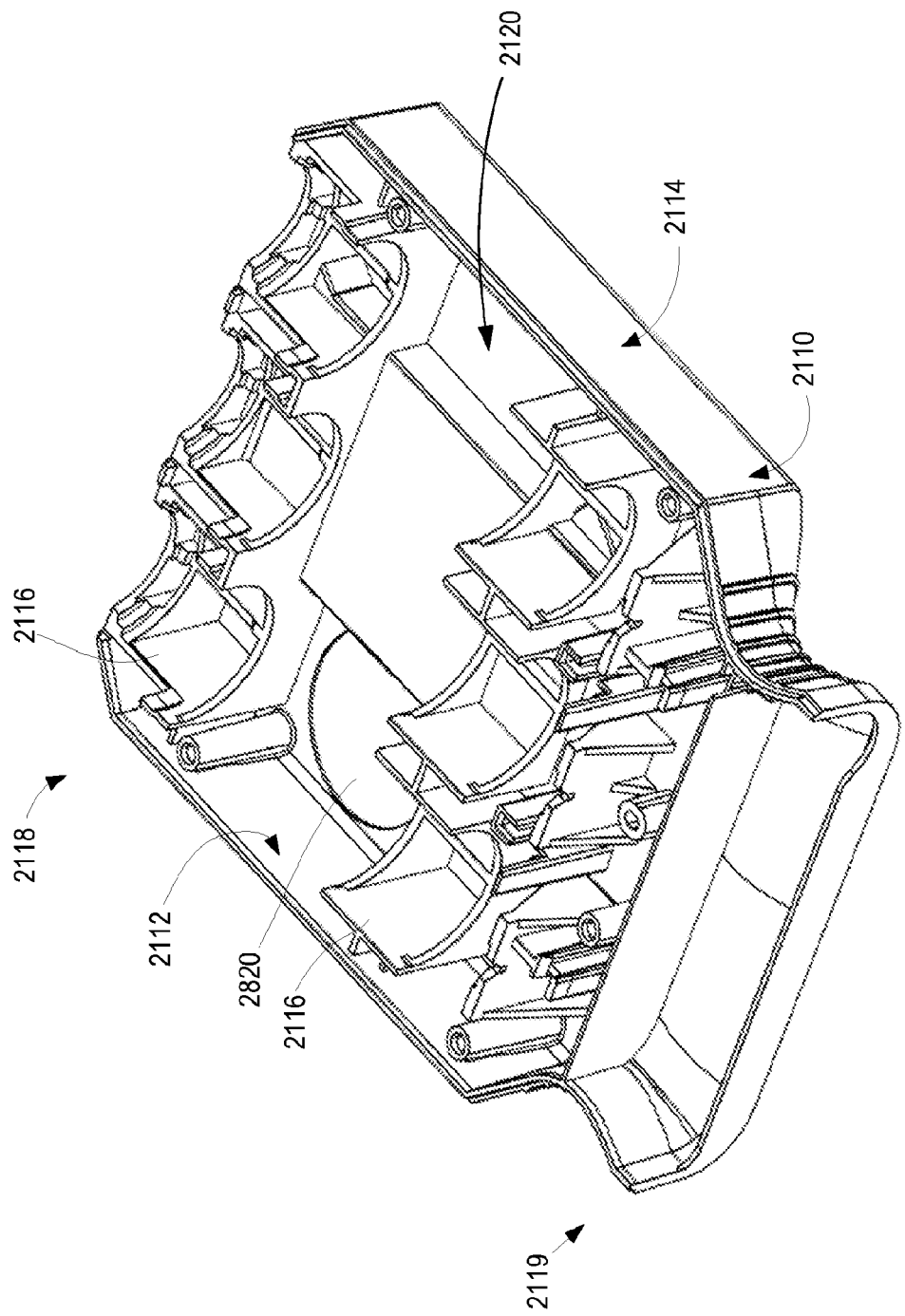
FIG. 13 is a perspective view of a first piece of the housing of the cartridge assembly of FIG. 2.
Figure 14:
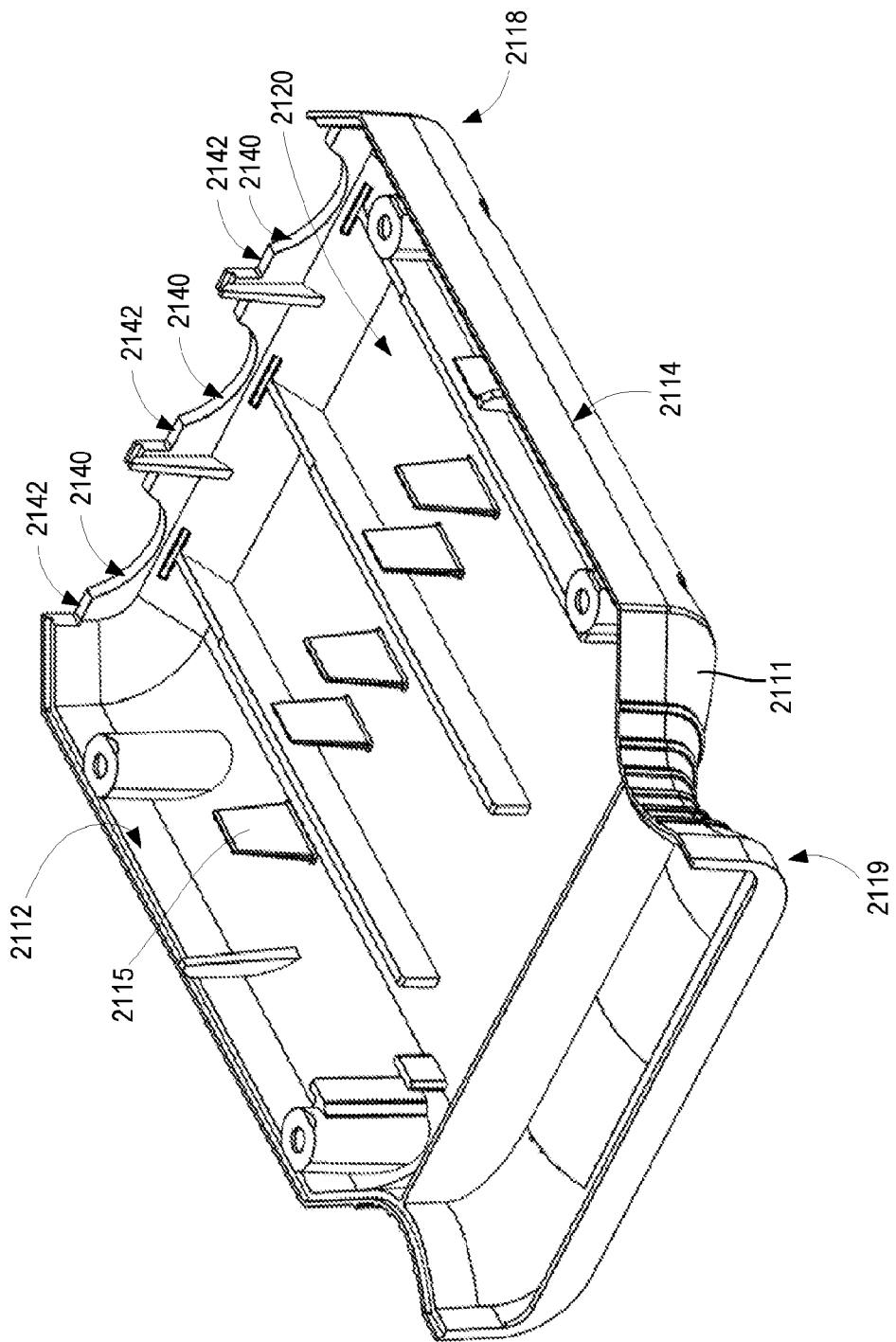
FIG. 14 is a perspective view of a second piece of the housing of the cartridge assembly of FIG. 2.

Referring to FIGS. 13 and 14, the cartridge assembly 2010 includes a first wall piece 2110 and a second wall piece 2111 that are coupled together to form a wall of the housing 2100. In some embodiments, the first wall piece 2110 is formed as an upper wall segment extending between a proximal portion 2118 and a distal end portion 2119 of the housing 2100. Similarly, the second wall piece 2111 can be formed as a lower wall segment extending between the proximal portion 2118 and the distal end portion 2119 of the housing 2100. The wall formed by the first wall piece 2110 and a second wall piece 2111 includes an inner face 2112. The inner face 2112 defines the internal volume 2120. In some embodiments, such as depicted in FIG. 7, the internal volume 2120 can include a first internal volume portion 2121 configured to receive the cartridges 2200. Additionally, the internal volume 2120 can include a second internal volume portion 2122. The second internal volume portion 2122 may be positioned proximally of the first internal volume portion 2121 and can receive the manifold assembly 2300 and/or the gate member 2500. The wall also defines a coil recess 2150 (see FIG. 7) that contains the tube set 2400 when the cartridge assembly 2010 is in a stored state $S_S$.

Figure 4:
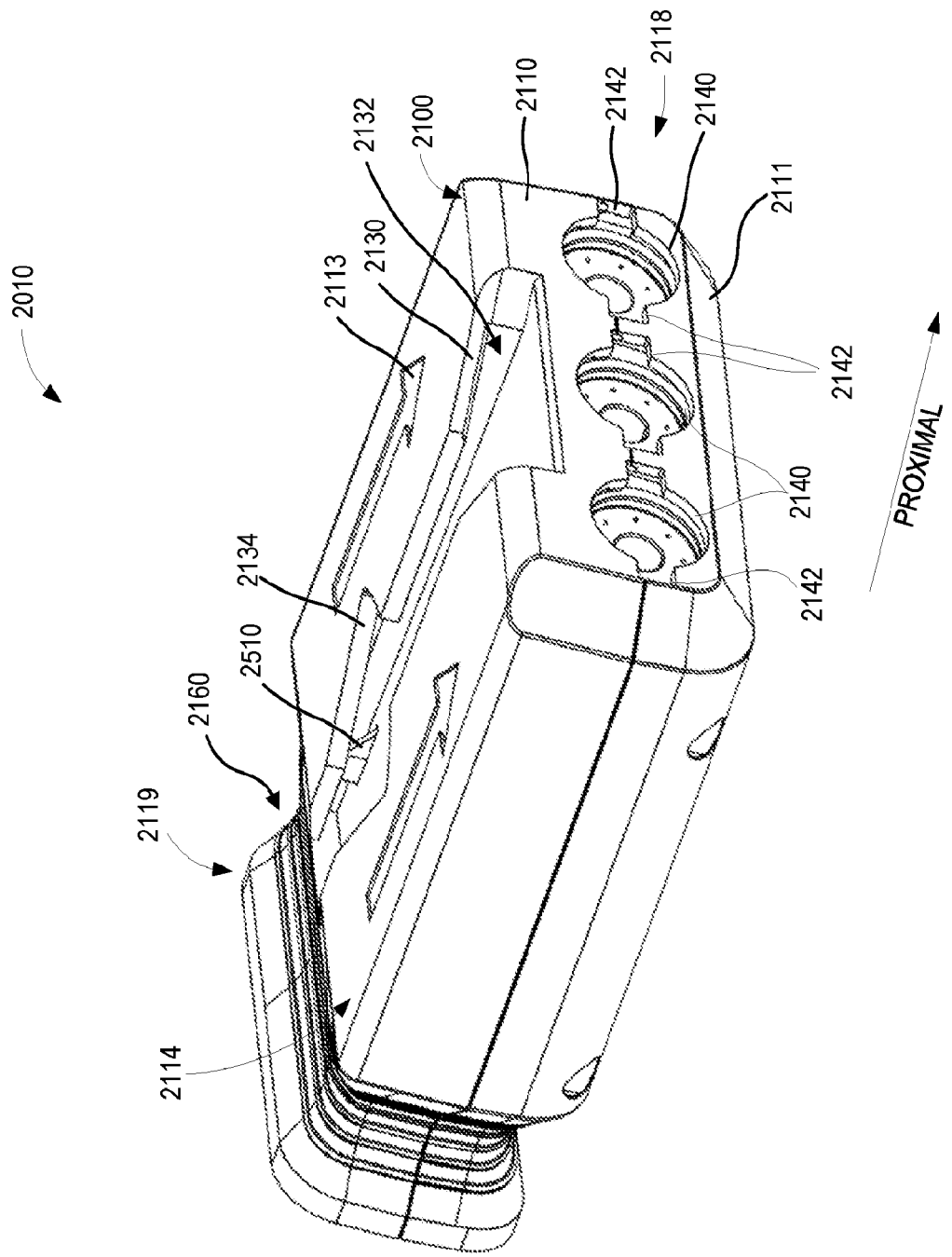
FIG. 4 is a perspective view of the cartridge assembly of FIG. 2.
Figure 5A:
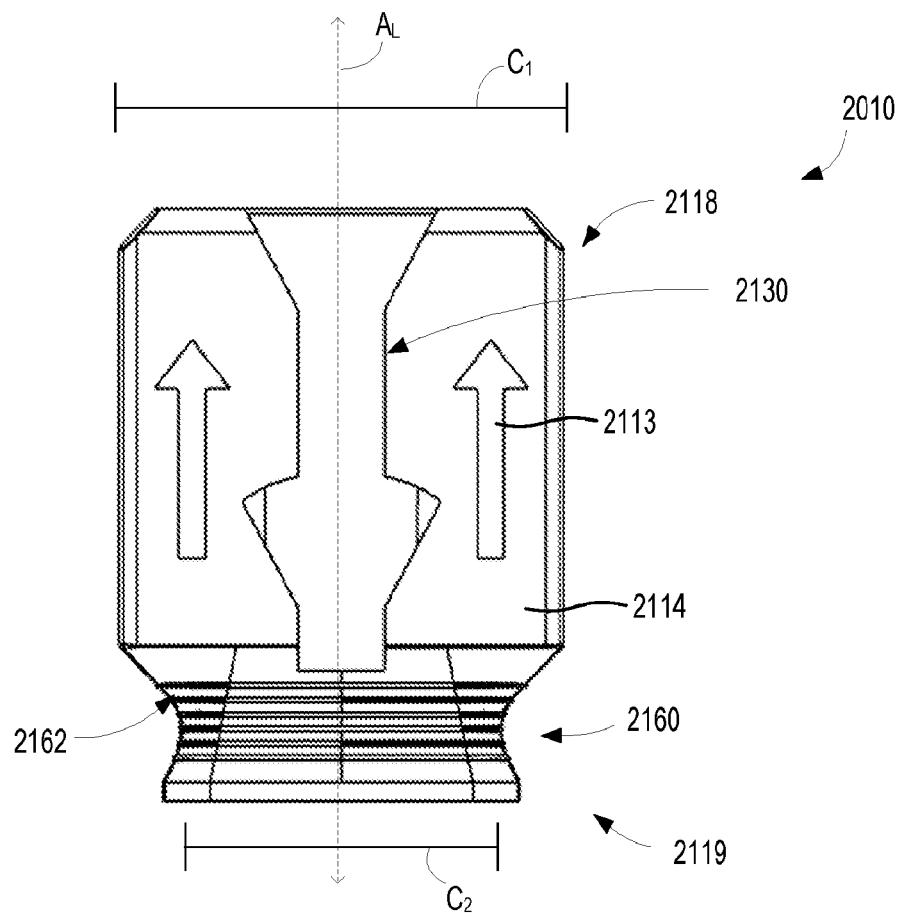
FIG. 5A is a top view of the cartridge assembly of FIG. 2.
Figure 5B:
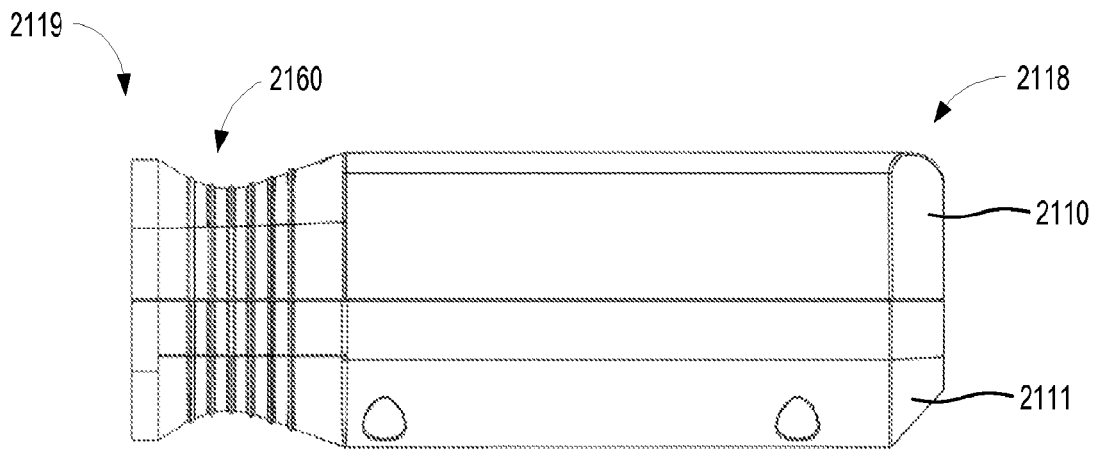
FIG. 5B is a side view of the cartridge assembly of FIG. 2.
Figure 27:
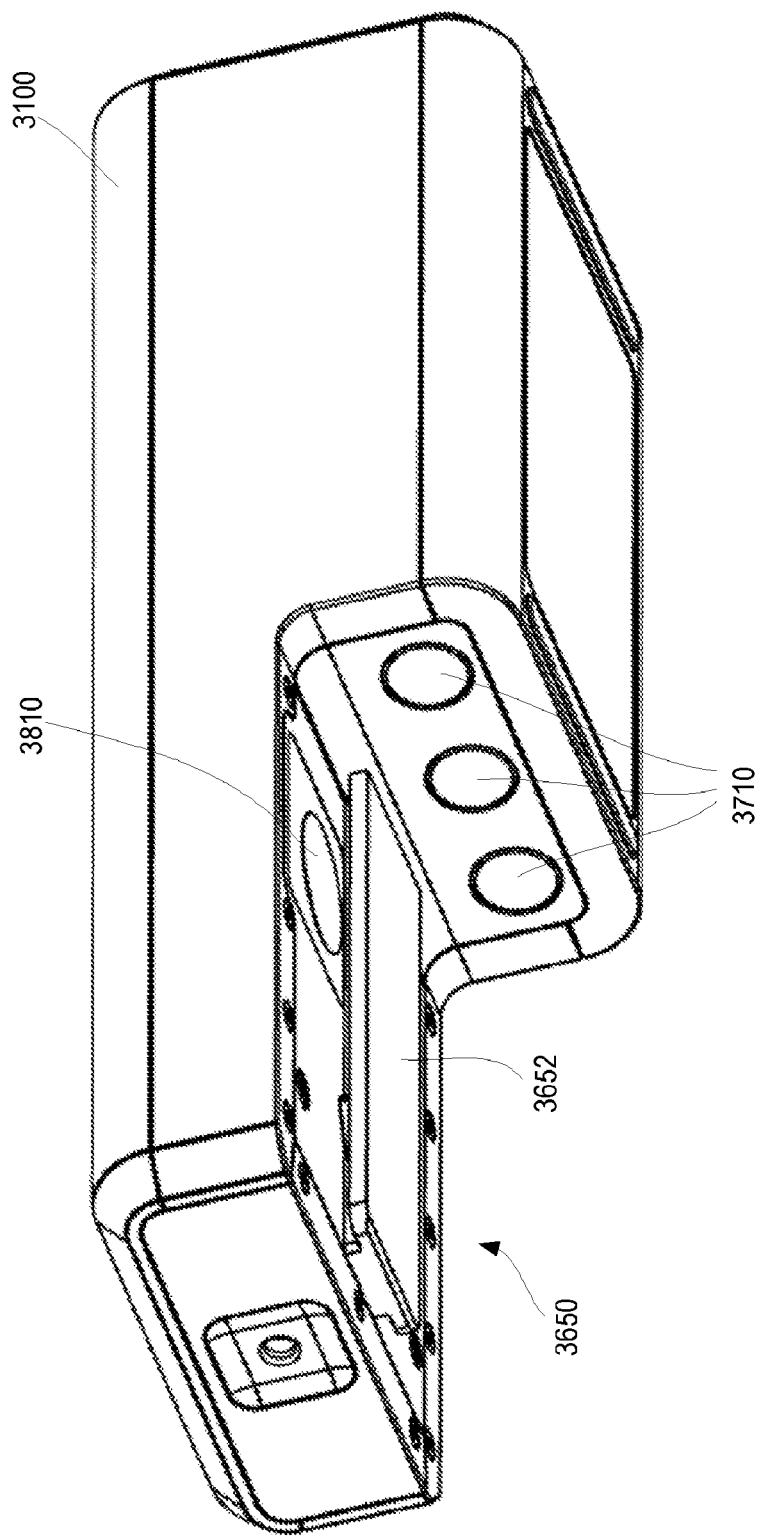
FIG. 27 is a perspective view of the pump assembly of the system of FIG. 26.
Figure 28:
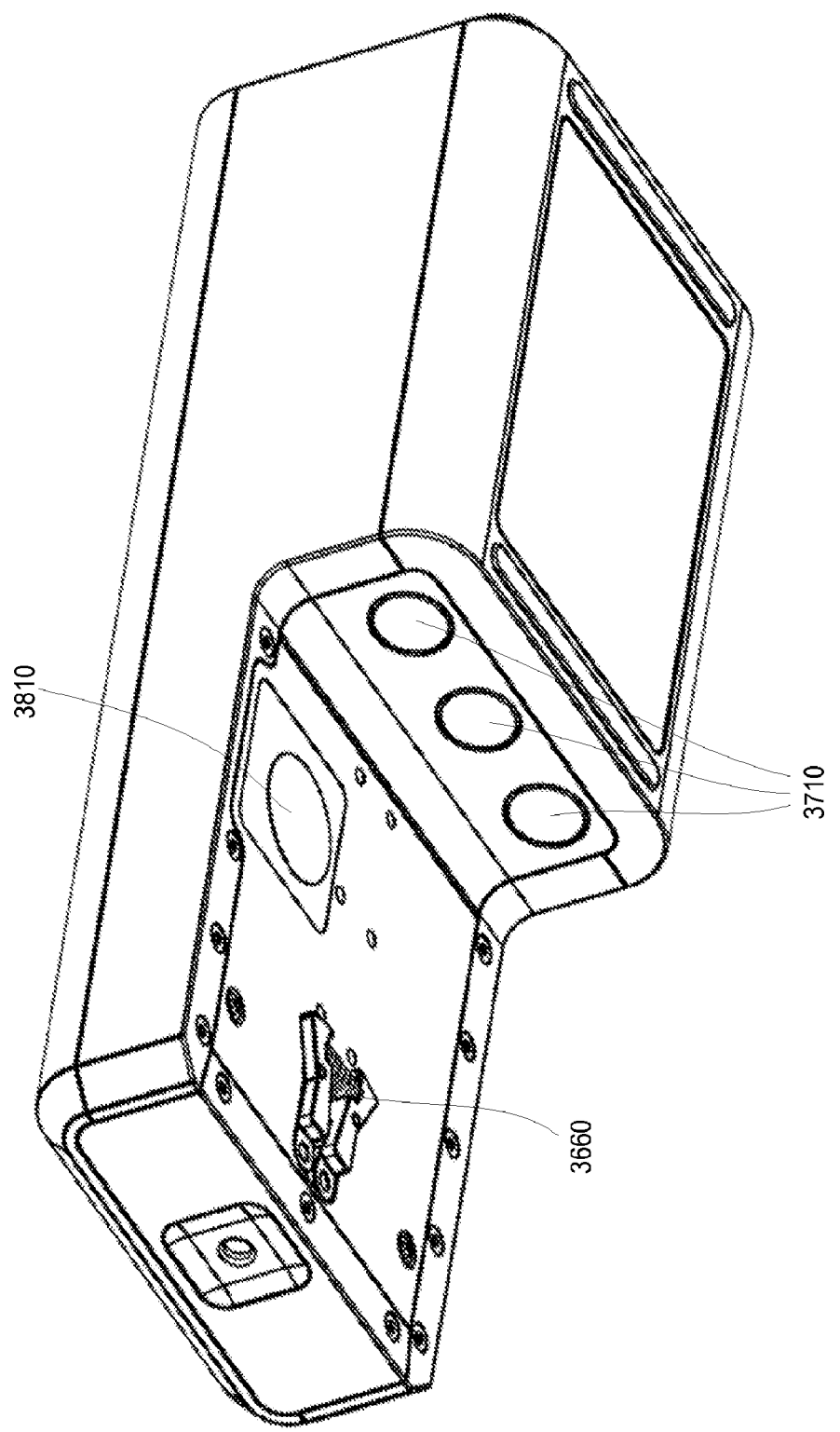
FIG. 28 is a perspective view of the pump assembly FIG. 26 with a protrusion of the coupling interface removed to show underlying features.

As depicted in FIG. 4 for example, an outer face 2114 of the wall (e.g., of the first wall piece 2110) includes the coupling member (or feature) 2130. The coupling feature 2130 includes a keyway 2132 and a receiver structure 2134. The keyway 2132 is configured to receive a mating coupling protrusion 2652 (FIG. 10) of the pump assembly 2020 (see, e.g., the coupling protrusion 3652 shown in in the pump of FIG. 27 configured as a T-track). The keyway 2132 includes a tapered opening (at the proximal end portion 2118 of the housing 2100) to facilitate easy coupling to the pump assembly 2020. The keyway 2132 also includes shoulders that are coupled within corresponding channels defined by the protrusion 2652 of the coupling interface 2650 to limit movement of the cartridge assembly 2010 relative to the pump assembly 2020 at least in any direction normal to the longitudinal axis $A_L$ of the cartridge assembly 2010. Similarly stated, the keyway 2132 can ensure that the access orifices 2140 are aligned with the corresponding drive members (e.g., pistons, not shown) of the pump assembly 2020. The keyway 2132 also ensures alignment of the actuation slots 2142 with the corresponding actuation members 2720 (FIG. 10) of the pump assembly 2020. In this manner, when the cartridge assembly 2010 is coupled to the pump assembly 2020, it will be aligned to facilitate accurate and repeatable actuation and delivery of medicament. The receiver structure 2134 includes two angular features having intersecting shoulders that are configured to mate with a latch member of the pump assembly 2020 (similar to the latch member 3660 shown in the pump assembly 3020 in FIG. 28). Thus, when the cartridge assembly 2010 is coupled to the pump, the latch member of the pump assembly 2020 will move outwardly and engage the receiver structure 2134. This engagement limits movement of the cartridge assembly 2010 relative to the pump assembly 2020 in a direction parallel to the longitudinal axis $A_L$ of the cartridge assembly 2010. In this manner, the axial position of the cartridge assembly 2010 can be fixed relative to the pump assembly 2020 during use, which enhances the accuracy of the dose delivered. In some embodiments, the outer face 2114 can include various markings 2113, such as arrows indicating a direction in which the cartridge assembly 2010 is moved to couple the cartridge assembly 2010 to the pump assembly 2020.

Figure 15:
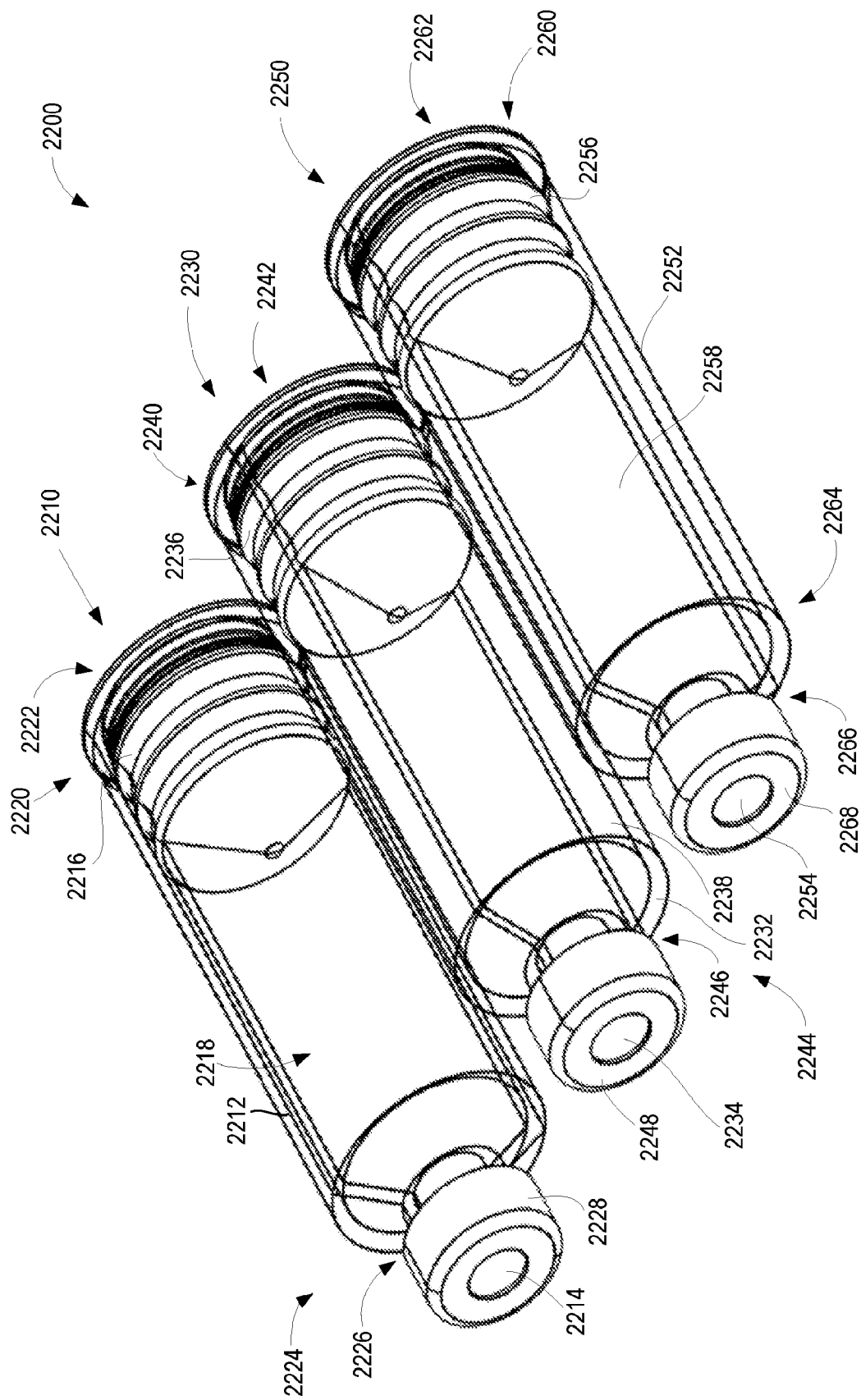
FIG. 15 is a perspective view of a set of cartridges of the cartridge assembly according to an embodiment.
Figure 16:
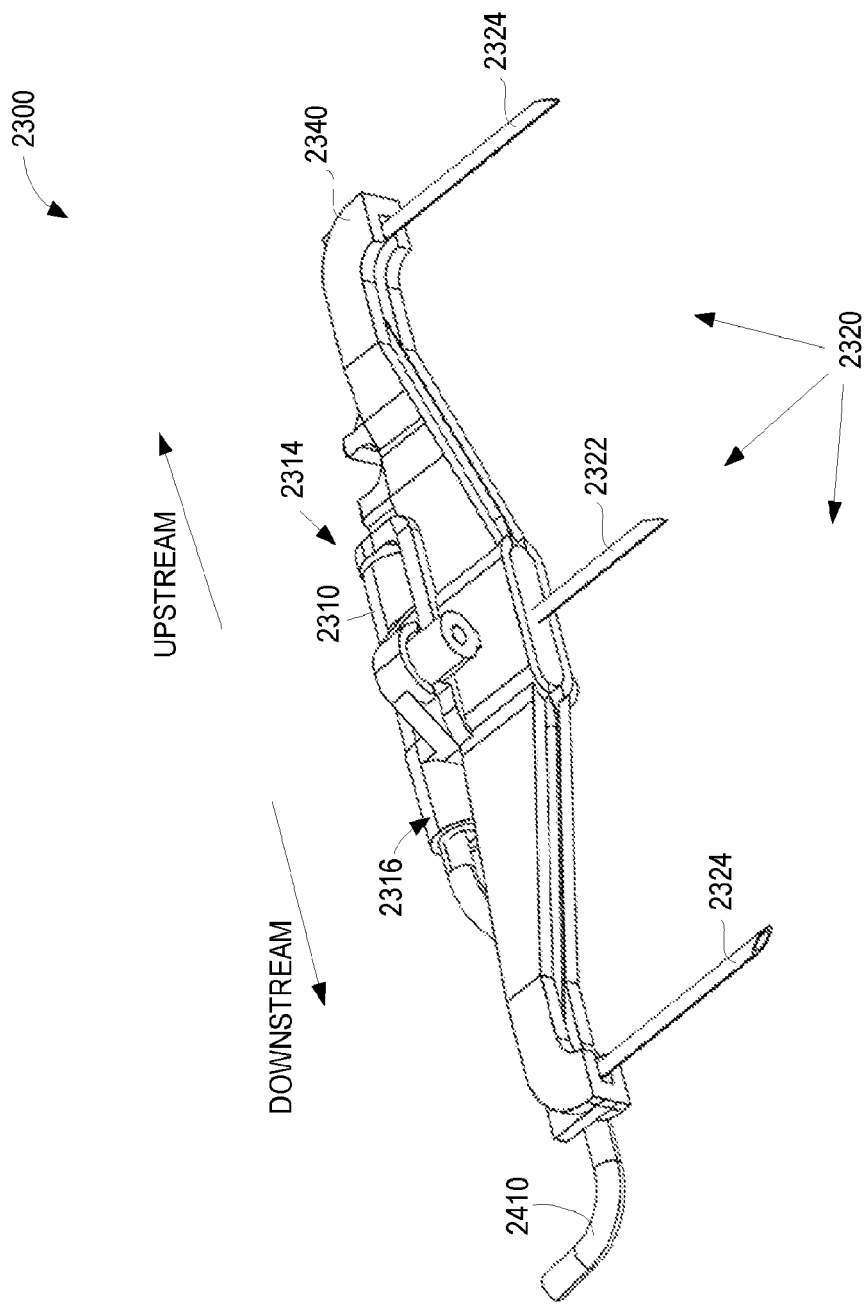
FIG. 16 is a perspective view of a manifold assembly of the cartridge assembly according to an embodiment.

Referring again to FIG. 13, the first wall piece 2110 is formed with multiple sets of cradles 2116 (one set at the proximal end portion 2118 and another set at the distal end portion 2119. The plurality of cradles 2116 are sized and positioned to at least partially surround the plurality of cartridges 2200. As such, the plurality of cradles 2116 can align and/or secure the plurality of cartridges 2200. Moreover, the set of cradles 2116 at the proximal end portion 2118 define a portion of a boundary of the access orifices 2140. Thus, when the first wall piece 2110 is coupled to the second wall piece 2111, the housing 2100 defines the set of access orifices 2140 that are aligned with the elastomeric members of each cartridge (e.g., the elastomeric members 2216, 2236, 2256 as shown in FIG. 15). Additionally, the first wall piece 2110 can include such other tabs, protrusions, rails and/or guides as are required to support any other components of the cartridge assembly 2010 positioned within the internal volume 2120.

In some embodiments, the first wall piece 2110 can also define and/or support a sensor interface 2820 for engaging with a sensing element 2810 (FIG. 3) of the pump assembly 2020. For example, the first wall piece 2110 can be formed with a recess into which the sensor interface 2820 may be inserted. The sensor interface 2820 can be any suitable feature that can operably engage with the sensing element, such as, for example, an RFID tag, an opening, a transparent region of the first wall piece 2110, a magnetic portion, a reflective region of the outer face, a colored region of the outer face 2114, and/or at least one protrusion, depression, or combination thereof.

Referring again to FIG. 14, the second wall piece 2111 is formed with a plurality of tapered ribs 2115. Each of the tapered ribs 2115 is deformable. Accordingly, the plurality of tapered ribs 2115 is deflected from a neutral position by the cartridges 2200 when the second wall piece 2111 is joined to the first wall piece 2110 during assembly of the cartridge assembly 2010. This deformation of the plurality of tapered ribs 2115 results in a force applied to each of the cartridges 2200 thereby securing the cartridges 2200 during transport and storage of the cartridge assembly 2010. The proximal end portion 2118 of the second wall piece 2111 also defines a portion of a boundary of the access orifices 2140 and the actuation slots 2142. Thus, when the first wall piece 2110 is coupled to the second wall piece 2111, the housing 2100 defines the set of access orifices 2140 that are aligned with the elastomeric members of each cartridge 2200. The housing 2100 also defines the actuation slots 2142 that can allow an actuation member 2720 of the pump assembly 2020 to exert a force on the container body (e.g., the first container body 2212, the second container body 2232, and/or the third container body 2252) of each cartridge 2200. In this manner, in some embodiments, a drive assembly 2700 of the pump assembly 2020 can exert a first force to move the cartridges 2200 within the housing 2100 (to place the cartridges in fluid communication with the manifold assembly 2300 that is independent from a second force that is exerted on the elastomeric member of each cartridge 2200 to cause delivery of the medicament therefrom. Additionally, the second wall piece 2111 can be formed with a status opening (see e.g., status opening 3117 as depicted in FIG. 30). The status opening can be utilized by a user of the cartridge assembly 2010 to verify the contents of the cartridge assembly 2010 before or after employment.

Figure 6B:
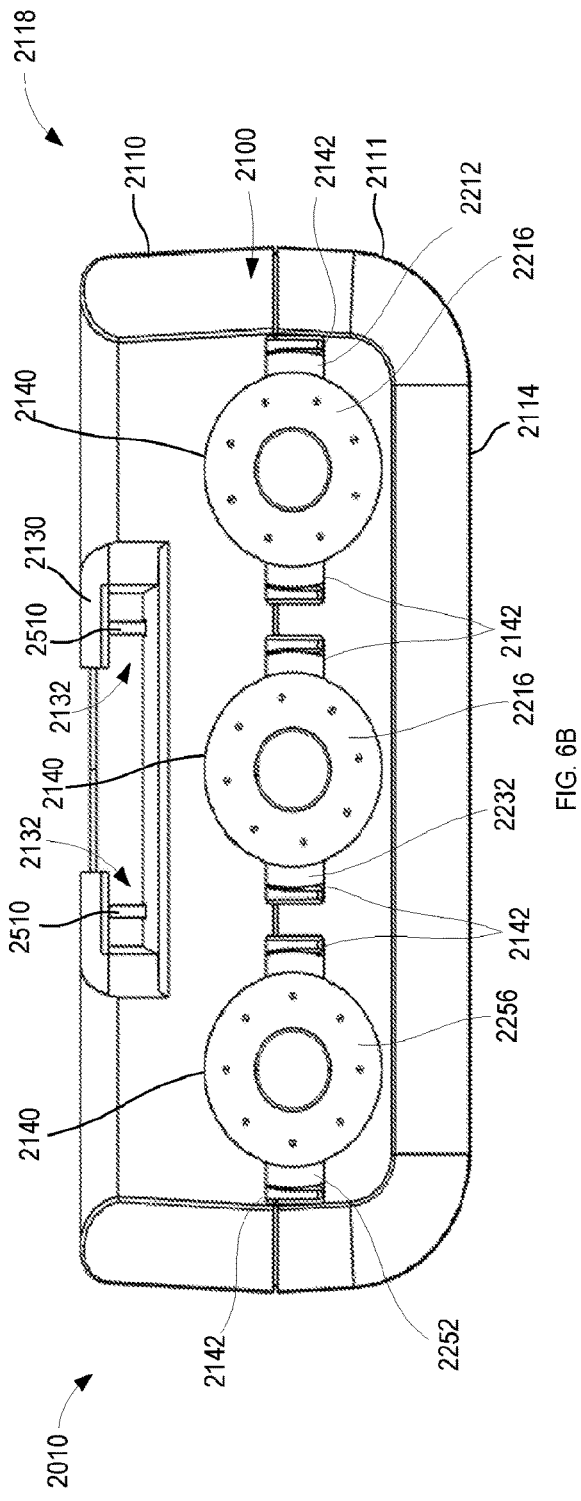
FIG. 6B is a rear view of the cartridge assembly of FIG. 2.

As depicted in FIGS. 4 and 6B, in some embodiments, the proximal end portion 2118 of the housing 2100 defines the actuation slots 2142. The actuation slots 2142 are configured to receive the actuation members 2720 of the pump assembly 2020 (see also FIG. 10). The actuation member 2720 is configured to transfer the first force to the first container body 2212, the second container body 2232, and/or the third container body 2252 transition the cartridges 2200 from a first longitudinal position $LP_1$ (See, e.g., FIG. 9) to a second longitudinal position $LP_2$ (See, e.g., FIG. 12) that is distal of the first longitudinal position $LP_1$ when the cartridge assembly 2010 is in an actuated state $S_A$ (also referred to as a second configuration).

Referring now to FIGS. 7, 8, 11, and 15, a first cartridge 2210 is positioned within the internal volume 2120. The first cartridge 2210 includes a first container body 2212. The first container body 2212 extends between a first container proximal end portion 2220 and a first container distal end portion 2224. The first container proximal end portion 2220 defines a first container opening 2222. The first container distal end portion 2224 includes a first container neck 2226. The first container neck 2226 is occluded by a first frangible seal 2214. The first frangible seal 2214 is coupled to the first container neck 2226 via a first aluminum crimp 2228. In some embodiments, the first aluminum crimp 2228 is color-coded or otherwise marked to be indicative of the contents of the first cartridge 2210. A first elastomeric member 2216 is disposed within the first container body 2212 to retain a portion of saline (e.g., a sodium chloride solution) 2218 within the first cartridge 2210.

As depicted, a second cartridge 2230 is positioned within the internal volume 2120. The second cartridge 2230 includes a second container body 2232. The second container body 2232 extends between a second container proximal end 2240 and a second container distal end portion 2244. The second container proximal end portion 2240 defines a second container opening 2242. The second container distal end portion 2244 includes a second container neck 2246. The second container neck 2246 is occluded by a second frangible seal 2234. The second frangible seal 2234 is coupled to the second container neck 2246 via a second aluminum crimp 2248. In some embodiments, the second aluminum crimp 2248 is color-coded or otherwise marked to be indicative of the contents of the second cartridge 2230. A second elastomeric member 2236 is disposed within the second container body 2232 to retain a portion of a first medicament 2238 within the second cartridge 2230.

In some embodiments, a third cartridge 2250 is positioned within the internal volume 2120. The third cartridge 2250 includes a third container body 2252. The third container body 2252 extends between a third container proximal end 2260 and a third container distal end portion 2264. The third container proximal end portion 2260 defines a container opening 2262. The third container distal end portion 2264 includes a third container neck 2266. The third container neck 2266 is occluded by a third frangible seal 2254. The third frangible seal 2254 is coupled to the third container neck 2266 via a third aluminum crimp 2268. In some embodiments, the third aluminum crimp 2268 is color-coded or otherwise marked to be indicative of the contents of the third cartridge 2250. A third elastomeric member 2256 is disposed within the third container body 2252 to retain a portion of a second medicament 2258 within the third cartridge 2250.

Referring now to FIGS. 16-21, the manifold assembly 2300 includes a manifold housing 2310, a manifold base 2340, a set of puncturers 2320, and a set of valves 2330. As described herein, the manifold assembly 2300 facilitates fluidically coupling each of the cartridges to a single volume (i.e., the receiving volume 2312) for delivery to the tube set 2400. The manifold housing 2310 defines a receiving volume 2312. The receiving volume 2312 has a sealed end portion 2314 and an output end portion 2316. The receiving volume 2312 also includes an input portion 2318 through which the contents of each of the cartridges can be conveyed into the receiving volume 2312. The sealed end portion 2314 may be sealed by a plug 2315 or any other suitable mechanism. For example, the manifold housing 2310 can be monolithically formed to include the sealed end portion 2314. The output end portion 2316 is coupled to a tube 2410 of the tube set at 2400. In some embodiments, the tube 2410 can be permanently fixed (e.g., glued) to the manifold housing 2310. As described in more detail below, this arrangement produces a direction of flow (see FIG. 17), with the first cartridge 2210 (containing saline) being coupled via the input portion 2318 at the upstream end of the receiving volume 2312 and the other cartridges being coupled via the input portion 2318 downstream from the entry of the first (i.e., saline) cartridge. In this manner, the saline flush from the first cartridge 2210 can flow through substantially the entire receiving volume 2312.

Figure 17:
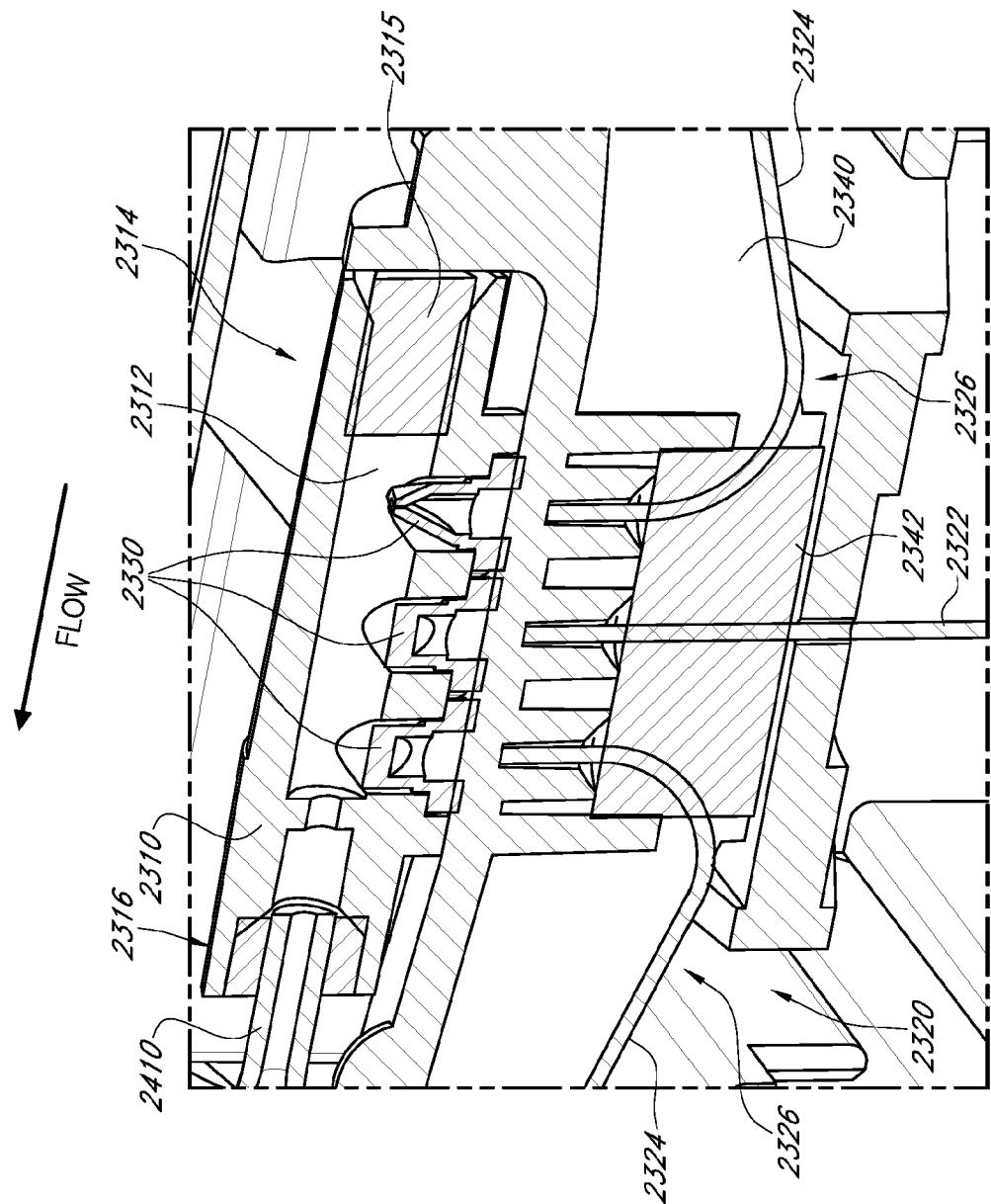
FIG. 17 is a cross-sectional view of a portion of the manifold assembly of FIG. 16.

As depicted, the manifold assembly 2300 also includes a manifold base 2340. The manifold base 2340 is coupled between the manifold housing 2310 and the cartridges 2200 and is coupled to the set of puncturers 2320. For example, as depicted in FIG. 17, a portion of each puncturers 2320 can be positioned within a recess defined by the manifold base 2340 and the recess can be filled with an adhesive 2342. Additionally, the manifold base 2340 can be a unitary body having a curvilinear face oriented to support the plurality of puncturers 2320.

The plurality of puncturers 2320 can be placed in fluid communication with the receiving volume 2312 via the set of valves 2330. The puncturers 2320 are oriented to puncture the frangible seals (e.g., the first frangible seal 2214, the second frangible seal 2234, and/or the third frangible seal 2254) occluding the distal end portions of each cartridge 2200. The puncturers 2320 can, for example, be needles or other similar structures able to convey a liquid therethrough. More specifically, the puncturers 2320 (or puncture assembly) can include a straight needle 2322 and at least one bent needle 2324. The size and curvature of the needles within the puncturer assembly is based on the desired size and spacing of the cartridges, and also the desired volume of the receiving volume 2312 of the manifold housing 2310. As described herein, to facilitate being able to accurately deliver a series of medicament doses in a timely manner and through a lengthy tube set, it can be desirable to minimize the overall volume of the system. Accordingly, by having a smaller (i.e., shorter length) receiving volume 2312, the manifold assembly 2300 includes different needles having various curvatures.

Figure 18:
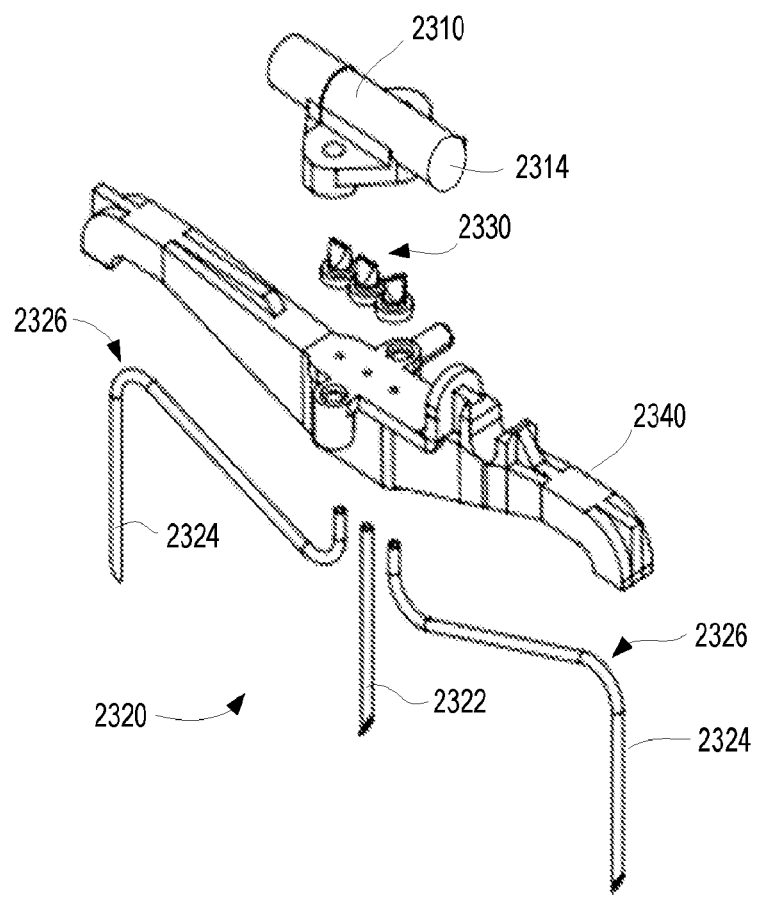
FIG. 18 is an exploded perspective view of the manifold assembly of FIG. 16.
Figure 19A:
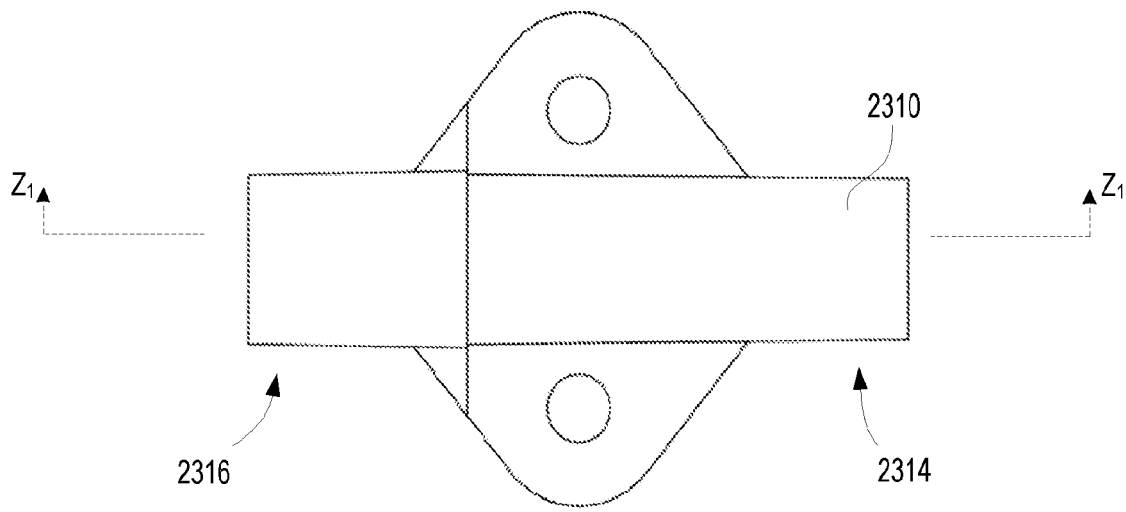
FIG. 19A is a top view of a manifold housing of the manifold assembly of FIG. 16.
Figure 19B:
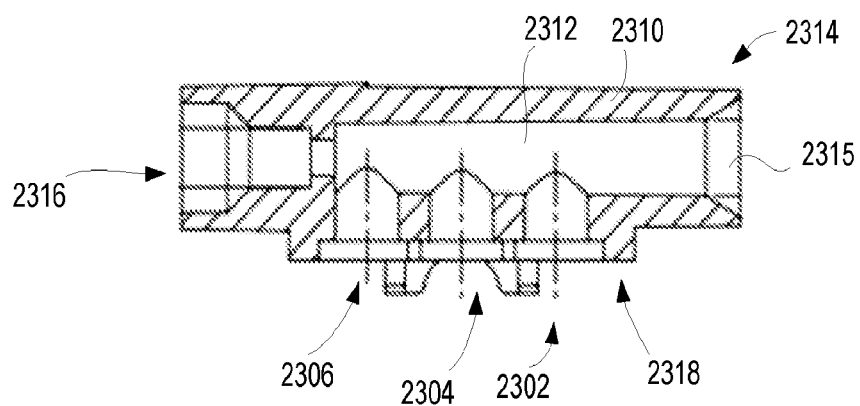
FIG. 19B is a cross-sectional view of the manifold housing of FIG. 19A taken at $Z_1$-$Z_1$.
Figure 20A:
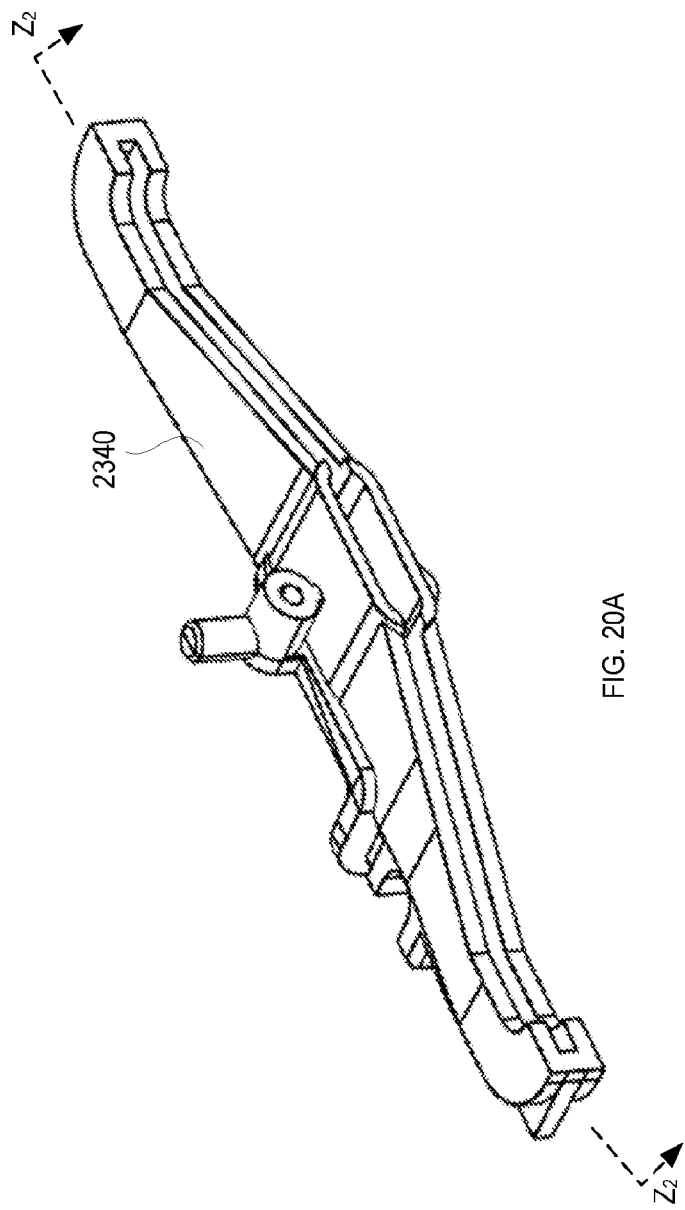
FIG. 20A is a perspective view of a manifold base of the manifold assembly of FIG. 16.
Figure 20B:
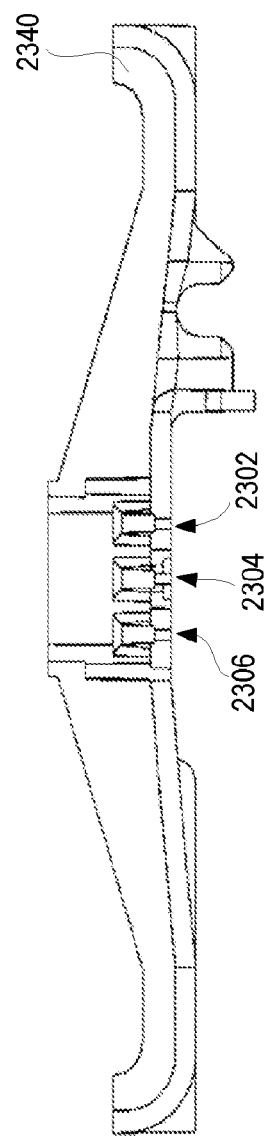
FIG. 20B is a cross-sectional view of the manifold base of FIG. 20A taken at $Z_2$-$Z_2$.
Figure 21:
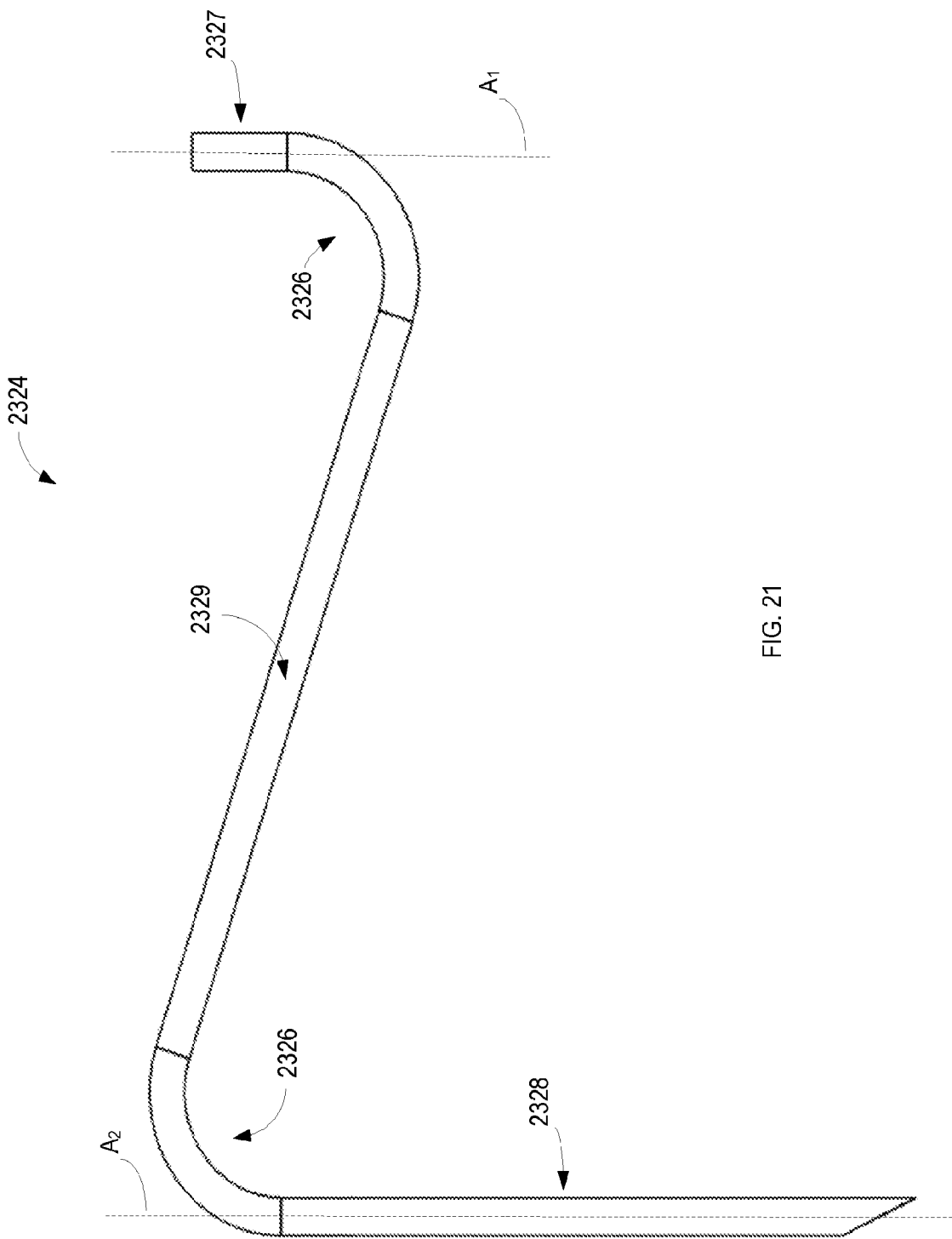
FIG. 21 is a top view of a bent needle of the manifold assembly of FIG. 16 according to an embodiment.

As depicted in FIGS. 18 and 21, the bent needle(s) 2324 includes a plurality of bends 2326. The bent needle(s) 2324 is a unitary structure that includes a distal portion 2327 and a proximal portion 2328 joined by a middle portion 2329. The distal portion 2327 is retained by the manifold base 2340. In some embodiments, the bend 2326 between the distal portion 2327 and the middle portion 2329 is proximal to the bend 2326 between the middle portion 2329 and the proximal portion 2328. The distal portion 2327 defines a first axis $A_1$. The proximal portion 2328 defines a second axis $A_2$. The first axis $A_1$ is parallel to the second axis $A_2$. However, first axis $A_1$ is displaced from the second axis $A_2$. For example, in some embodiments, the second axis $A_2$ is displaced laterally relative to the first axis $A_1$. It should be appreciated that the plurality of bends 2326 facilitate both the fluid communication with a receiving volume 2312 and an axial alignment of the proximal portion 2328 with a cartridge 2200 (e.g., the first cartridge 2210 or the third cartridge 2350) that is laterally displaced away from the longitudinal axis $A_L$ defined by the housing 2100.

As depicted in FIGS. 17 and 18, the manifold assembly 2300 includes a set of one-way valves 2330. The one-way valves 2330 are disposed between the puncturers 2320 and the receiving volume 2312. The one-way valves 2330 can be an elastomeric valve that permits forward flow while preventing backflow. For example, the one-way valves 2330 can be duckbill valves in which the sealing function is an integral part of the one-piece elastomeric valve. The one-way valves 2330 default to a closed (e.g., sealed) state in the absence of a forward flow. The utilization of the one-way valves 2330 precludes the contents of any of the cartridges 2200 from being introduced to another cartridge 2200 during delivery. Said another way, the one-way valves 2330 permit a fluid flow from the corresponding puncturers 2320 only in the direction of the receiving volume 2312 and do not permit a flow from the receiving volume 2312 to any of the puncturers 2320 and on to the cartridges 2200. As depicted, the one-way valves 2330 are disposed along the input portion 2318 of the manifold housing 2310. Accordingly, the sealed end portion 2314 is upstream of the one-way valves 2330.

The arrangement of the puncturers 2320, as retained by the manifold base 2340, determines a coupling location for each cartridge 2200 relative to the manifold housing 2310. The first cartridge 2210 is fluidically coupled to the receiving volume 2312 at coupling location 2302, which is upstream of all other coupling locations. The second cartridge 2230 is fluidically coupled to the receiving volume at coupling location 2304, which is downstream of the coupling location 2302. Further, the third cartridge 2250 is fluidically coupled to the receiving volume at coupling location 2306, which is downstream of both coupling location 2302 and coupling location 2304. In so far as the first cartridge 2210 contains the portion of saline 2218, the portion of saline 2218 can be introduced to the receiving volume 2312 at a point that is upstream of any medicament. Accordingly, saline introduced to the receiving volume 2312 at coupling location 2302 will flush any medicament within the receiving volume 2312 toward the tubes that 2400 and on to the patient. It should be appreciated that the introduction of the saline upstream of the medicament can ensure that the entirety of the prescribed dose is accurately delivered to the patient rather than being retained in a volume of the manifold assembly 2300 and/or the tube set 2400.

As depicted in FIGS. 7-10, prior to the actuation of the cartridge assembly 2010, a separation distance SD is maintained between the puncturers 2320 and the plurality of cartridges 2200. In other words, the proximal end of each of the puncturers 2320 is separated from a corresponding axially-aligned frangible seal (e.g., the first frangible seal 2214, the second frangible seal 2234, and/or the third frangible seal 2254) prior to the actuation of the cartridge assembly 2010. However, as depicted in FIGS. 11 and 12, when the cartridge assembly 2010 is in an actuated state $S_A$, the plurality of cartridges 2200 are fluidically coupled to the receiving volume 2312 via the plurality of puncturers 2320. In the actuated state $S_A$, the proximal end of each of the puncturers 2320 penetrates the corresponding frangible seal and enters a volume defined by container body of the corresponding cartridge 2200. In other words, the first cartridge 2210 and the second cartridge 2230 are fluidically coupled to the receiving volume 2312 via the plurality of puncturers 2320 when the cartridge assembly 2010 is in the actuated state $S_A$. In some embodiments, the first cartridge 2210, the second cartridge 2230, and the third cartridge 2250 are fluidically coupled to the receiving volume 2312 via the plurality of puncturers 2320 when the cartridge assembly 2010 is in the actuated state $S_A$. In other embodiments, the puncturers and/or cartridges can be moved sequentially so that one of the cartridges is fluidically coupled to the receiving volume 2312 while another of the cartridges remains fluidically isolated from the receiving volume 2312. Similarly stated, in some embodiments, the cartridge assembly 2010 can have multiple different actuated states, each actuation state corresponding to a different cartridge being fluidically coupled to the receiving volume 2312.

The coupling location 2302 (FIG. 19B) of the first cartridge 2210 is upstream of the coupling location 2304 (FIG. 19B) of the second cartridge 2230 and the coupling location 2306 (FIG. 19B) of the third cartridge 2350. In such an orientation, a bolus of saline dispensed from the first cartridge 2210 upstream of a dose of the first medicament 2238 or the second medicament 2258 ensures that the entirety of the dose of the first medicament 2238 or the second medicament 2258 is cleared from the manifold assembly 2300 and the tube set 2400 and delivered to the patient. It should be appreciated that the second medicament 2258 contained by the third cartridge 2250 can be different from the first medicament 2238 contained by the second cartridge 2030.

Referring now to FIGS. 9 and 12, the housing 2100 defines the longitudinal axis $A_L$. The longitudinal axis $A_L$ extends along a long axis of the housing 2100 in the proximal direction and in the distal direction. In some embodiments, the longitudinal axis $A_L$ corresponds to a central axis of the cartridge assembly 2010. The manifold assembly 2300 is at the fixed longitudinal position $LP_F$ when the cartridge assembly 2010 is in a stored state $S_S$, as depicted in FIG. 9. The manifold assembly 2300 is at the fixed longitudinal position $LP_F$ when the cartridge assembly 2010 is in the actuated state $S_A$, as depicted in FIG. 12. Said another way, the manifold assembly 2300 is at the same fixed longitudinal position $LP_F$ when the cartridge assembly 2010 is in both the stored state $S_S$ and the actuated state $S_A$. With this arrangement, the cartridges (and not the manifold assembly) move within the housing 2100, as described below, to transition the cartridge assembly 2010 from the stored state $S_S$ (or a first configuration, in which the cartridge assembly 2010 is within the pump assembly 2020 but is not actuated) to the actuated state $S_A$ (or a second configuration, in which the cartridge assembly is both coupled to the pump assembly 2020 and one or more cartridges is fluidically coupled to the manifold assembly 2300).

Referring still to FIGS. 9 and 12, in some embodiments, the plurality of cartridges 2200 are movable within the internal volume 2120. As such, the plurality of cartridges 2200 are at a first longitudinal position $LP_1$ when the cartridge assembly 2010 is in the stored state $S_S$. The plurality of cartridges 2200 are at a second longitudinal position $LP_2$ when the cartridge assembly 2010 is in the actuated state $S_A$. The second longitudinal position $LP_2$ is distal to the first longitudinal position $LP_1$. Said another way, the first cartridge 2210, the second cartridge 2230, and the third cartridge 2250 are movable within the internal volume 2120. The first cartridge 2210, the second cartridge 2230, and the third cartridge 2250 are at the first longitudinal position $LP_1$ when the cartridge assembly 2010 is in the stored state $S_S$ and at the second longitudinal position $LP_2$ that is distal to the first longitudinal position $LP_1$ when the cartridge assembly 2010 is in the actuated state $S_A$.

As depicted in FIGS. 8 and 9, the gate member 2500 is positioned within the internal volume 2120. When in a locked position $P_L$ (e.g., a locked orientation, an extended orientation, an initial orientation, or a nominal position), the gate member 2500 maintains the separation distance SD between the plurality of puncturers 2320 and the frangible seals of the plurality of cartridges 2200, as described in more detail below. The gate member 2500 is in the locked position $P_L$, as depicted in FIGS. 8 and 9, when the cartridge assembly 2010 is in the stored state $S_S$.

Figure 23:
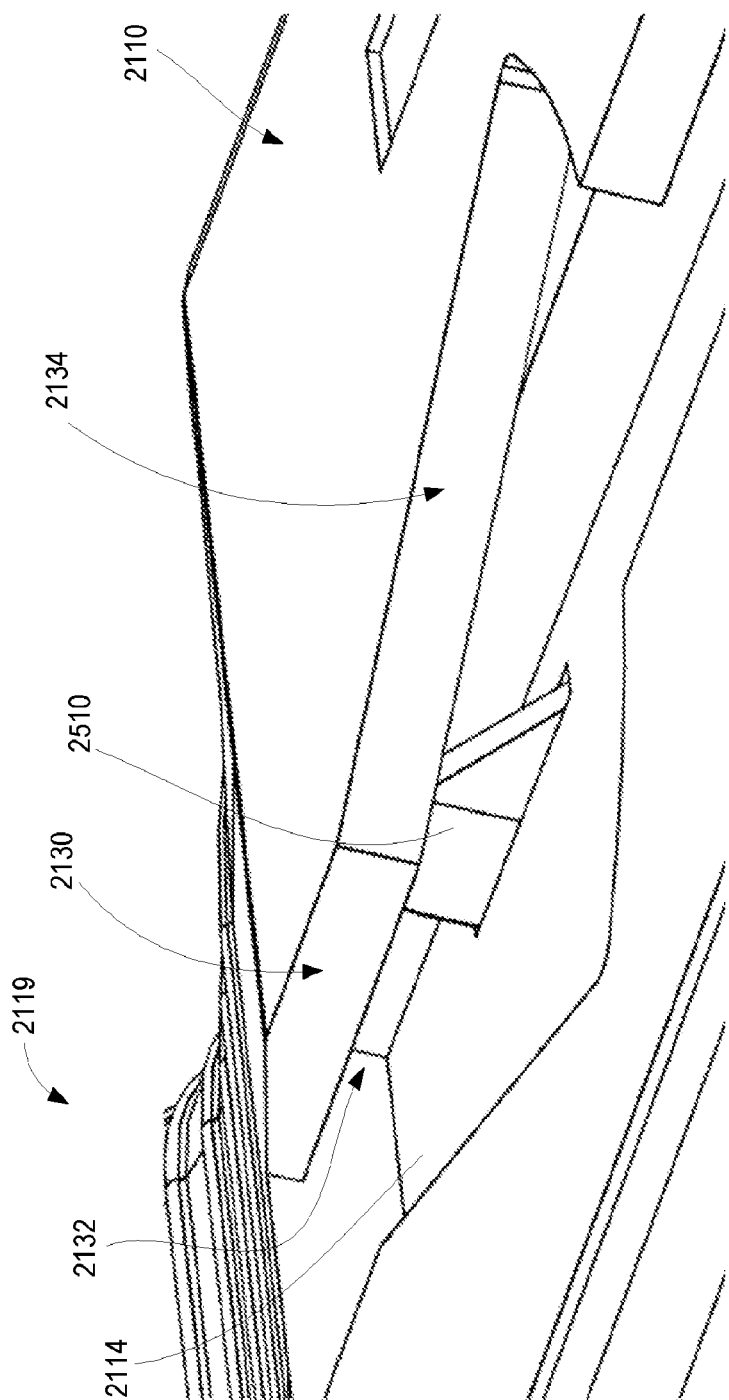
FIG. 23 is a perspective view of a portion of the cartridge assembly of FIG. 4 showing a portion of the gate member extending through an opening in the cartridge housing.

In the lock position $P_L$, the gate member 2500 has an actuation portion 2510 that is at a position between the outer face 2114 and the coupling member 2130 as depicted in FIGS. 4 and 23. In other words, the actuation portion 2510 extends from the internal volume 2120 through the first wall piece 2110. The actuation portion 2510 is positioned such that when the cartridge assembly 2010 is coupled to the pump assembly 2020, the actuation portion 2510 is engaged by a protrusion 2652 of the coupling interface 2650 of the pump assembly 2020, as depicted in FIG. 10. The engagement of the actuation portion 2510 by the protrusion 2652 transitions the gate member 2500 from the locked position $P_L$ to an unlocked position $P_U$. For example, as depicted in FIGS. 10-12, the transition to the unlocked position $P_U$ corresponds to a movement of the gate member 2500 toward the second wall piece 2111 (e.g., a movement away from the coupling interface 2650). Although the actuation portion 2510 is shown as including two protrusions that extend from the internal volume 2120, in other embodiments, an actuation portion can include any structure that extends from the housing 2100 to be actuated when the cartridge assembly 2010 is coupled to the pump assembly 2020.

Figure 22:
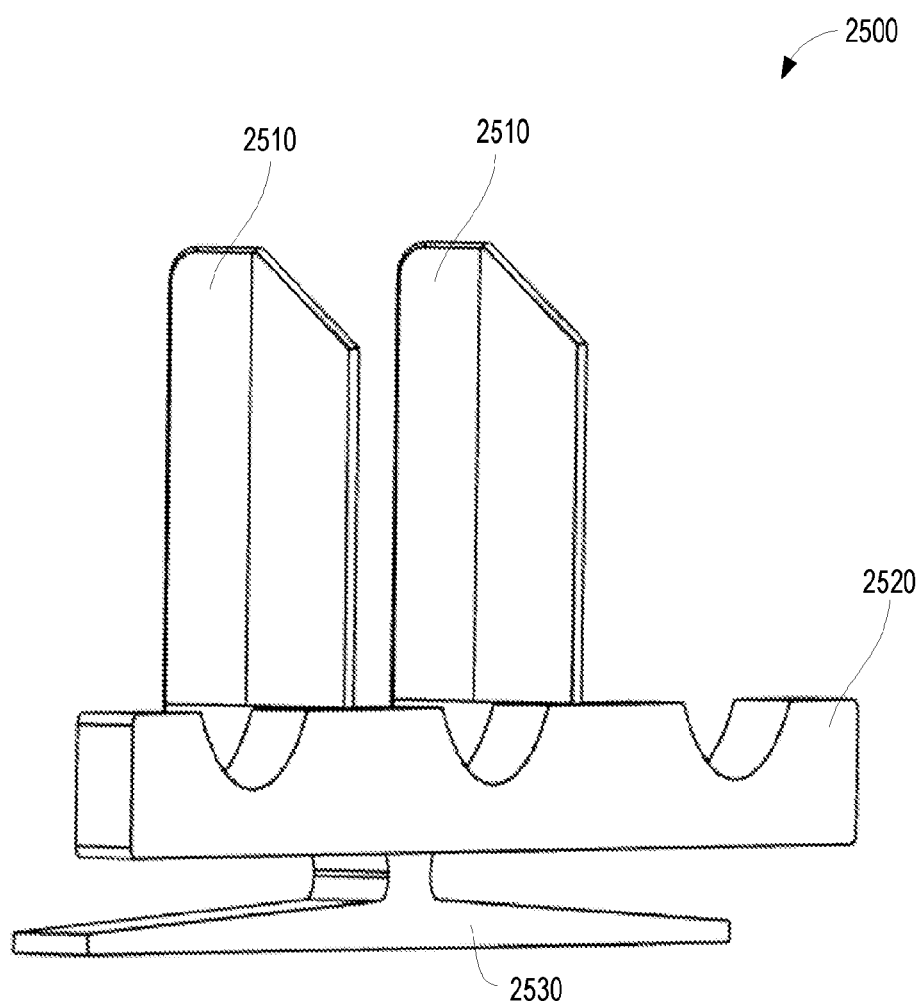
FIG. 22 is a perspective view of a gate member of the cartridge assembly according to an embodiment.

Referring to FIGS. 8-12, the gate member 2500 includes an engagement member 2520. The engagement member 2520 is a substantially stiff structure that is oriented to engage the plurality of cartridges 2200. For example, the engagement member 2520 can be a beam structure that is oriented perpendicular to the longitudinal axis $A_L$. As such, the engagement member 2520 is oriented to engage the first cartridge 2210 and the second cartridge 2230. When the gate member 2500 is in the locked position $P_L$, the engagement member 2520 limits a movement of the plurality of cartridges 2200 from the first longitudinal position LP$_1$, such as depicted in FIGS. 8-10, in a distal direction. Said another way, the interaction of the proximal face of engagement member 2520 with the first aluminum crimp 2228, the second aluminum crimp 2248, and/or the third aluminum crimp 2268 precludes movement of the first cartridge 2210, the second cartridge 2230, and/or the third cartridge 2250 from the first longitudinal position LP$_1$ to the second longitudinal position LP$_2$, such as depicted in FIGS. 11 and 12. Similarly stated, when the gate member 2500 is in the locked position P$_L$, the proximal face of the engagement member 2520 is between the proximal-most tip of the puncturers and the distal most portion of the aluminum crimps of the cartridges. As depicted in FIG. 22, the engagement member 2520 can be formed with a plurality of cutouts to facilitate the distal movement of the plurality of cartridges 2200 when the gate member 2500 is in the unlocked position P$_U$.

Referring still to FIGS. 8 to 12, the gate member 2500 includes at least one spring element (or portion) 2530. The spring element(s) 2530 is positioned between the engagement member 2520 and the inner face 2112 of the wall. The spring element(s) 2530 biases the engagement member 2520 in (e.g., toward) the locked position P$_L$ when the cartridge assembly 2010 is in the stored state S$_S$. In other words, the spring element(s) 2530 exerts a force on the engagement member 2520 toward the first wall piece 2110 when the actuation portion 2510 is in a nominal position (e.g., not engaged by the protrusion 2652). Accordingly, when the actuation portion 2510 is engaged by the protrusion 2652 and the gate member 2500 transitions to the unlock position P$_U$, the spring element(s) 2530 is compressed.

As depicted in FIG. 22, in some embodiments, the gate member 2500 is a unitary structure. In such an embodiment, the spring element(s) 2530 includes spring arms that are formed during the manufacture of the gate member 2500 from the same material as the gate member 2500. However, in other embodiments, the spring element(s) 2530 can be a leaf spring, a coil spring, or an elastomeric structure that is positioned between the engagement member 2520 and the inner face 2112.

In some embodiments, the actuation portion 2510 extends from the engagement member 2520 to the position between the outer face 2114 and the coupling member 2130. Said another way, in some embodiments, the actuation portion 2510 of the gate member 2500 is positioned within the keyway 2132 as depicted in FIG. 23. In some embodiments, the gate member 2500 includes more than one actuation portion 2510. For example, as depicted in FIG. 22, the gate member 2500 includes two actuation portions 2510 that extend perpendicularly from the engagement member 2520 in parallel. In some embodiments wherein the gate member 2500 is a unitary structure, the actuation portion 2510 is formed during the manufacture of the gate member 2500 from the same material. Similarly stated, in some embodiments the gate member 2500 including the spring element(s) 2530 and the actuation portion 2510 is monolithically constructed. In other embodiments, the engagement member 2520, the spring element(s) 2530, and/or the actuation portion 2510 can be formed separately and the coupled together to form the gate member 2500.

As described herein, the cartridge assembly 2010 is operably coupled to a medical port (not shown) via the tube set 2400. When the cartridge assembly 2010 is in the stored state S$_S$, the tube set 2400 is contained within a coil recess 2150 defined by the housing 2100. As depicted in FIG. 6A, the housing 2100 defines an opening 2163 to the coil recess 2150 at the distal end portion 2119 of the housing 2100. In some embodiments, the opening 2163 can be occluded by a removable cover (not shown). For example, the removable cover can be a peel-away seal that is removed in order to access the tube set 2400. In some embodiments, the removable cover can be coupled to the tube set 2400 so that removal of the removable cover can facilitate the extraction of a portion of the tube set from the coil recess 2150.

Figure 24:
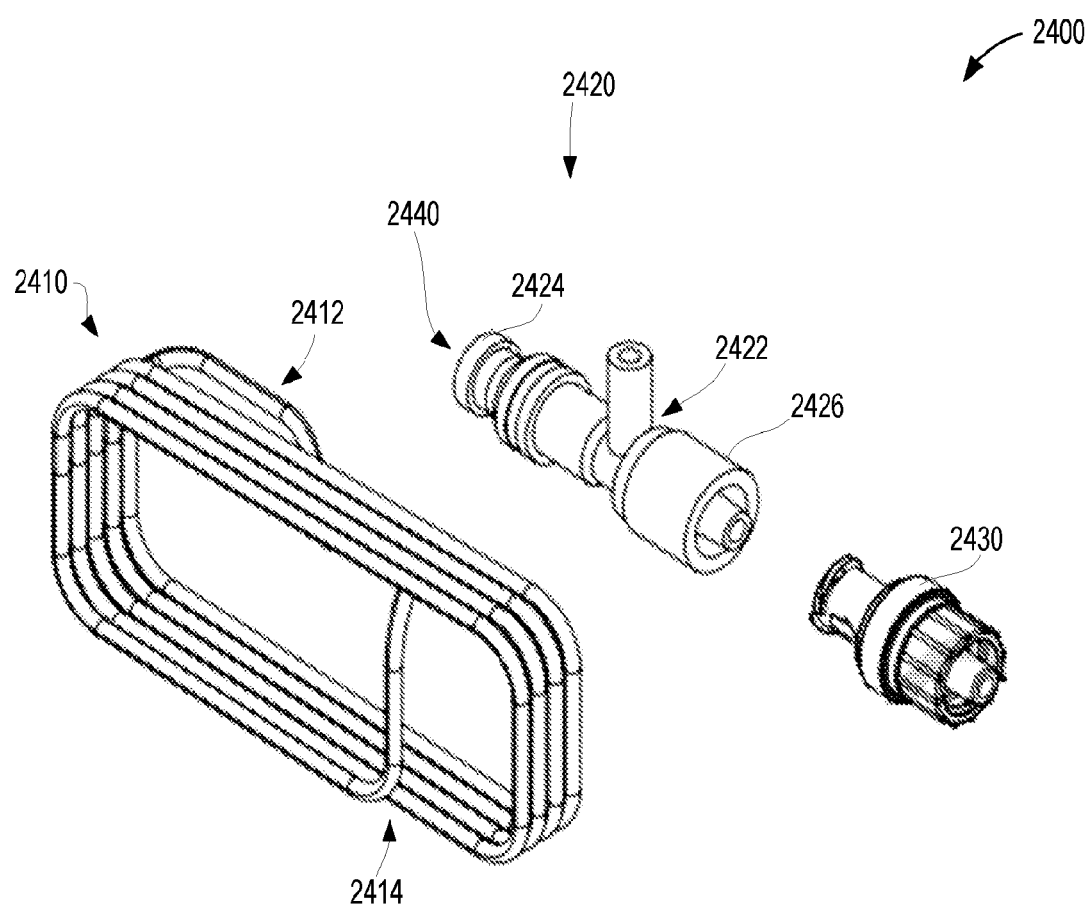
FIG. 24 is a perspective view of a tube set of the cartridge assembly of FIG. 2 according to an embodiment.
Figures 25A, 25B:
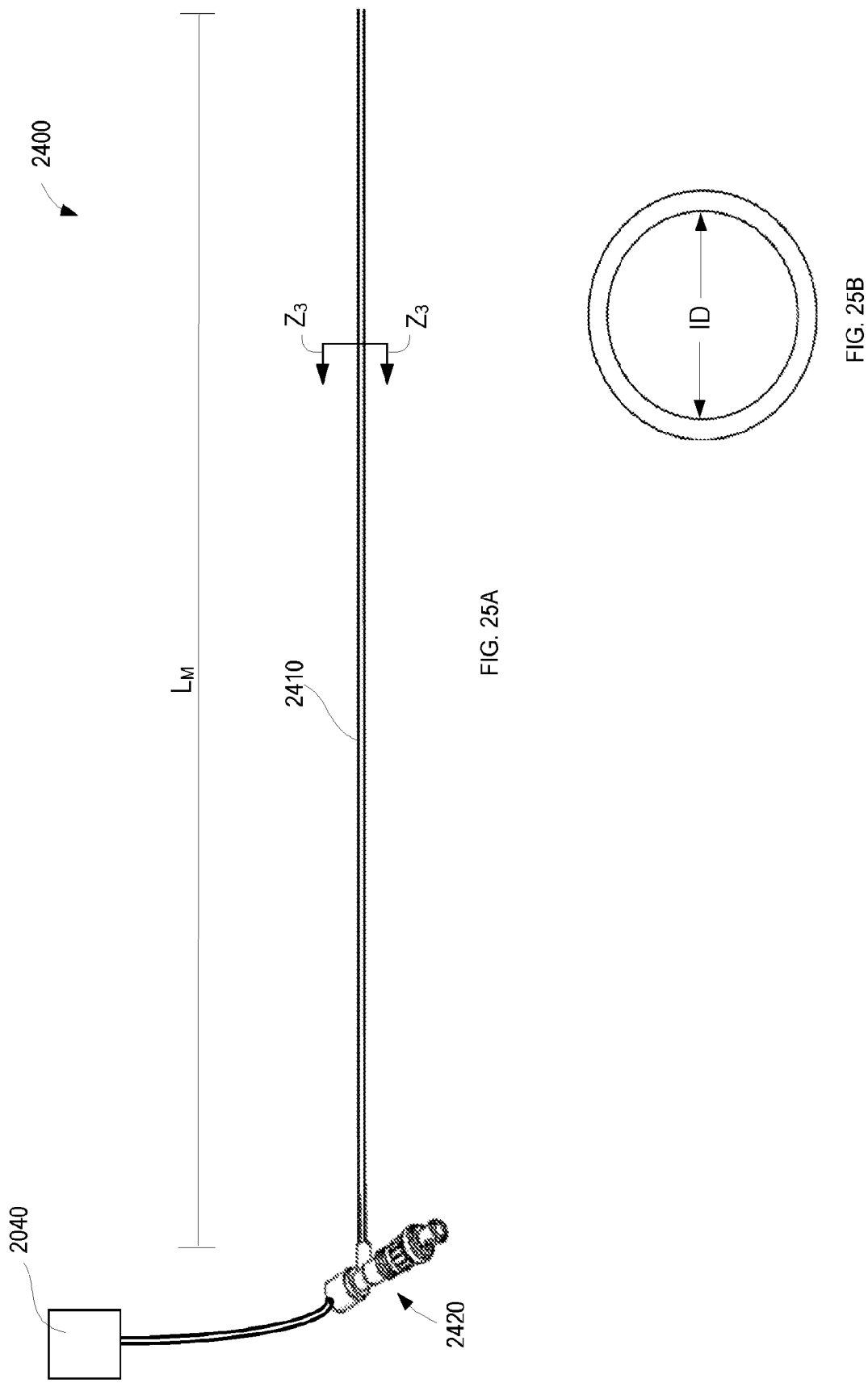
FIG. 25A is a perspective view of the tube set of FIG. 24 illustrating the tube in an uncoiled orientation.
FIG. 25B is a cross-sectional view of the tube of FIG. 25A taken at $Z_3$-$Z_3$.
Figure 26:
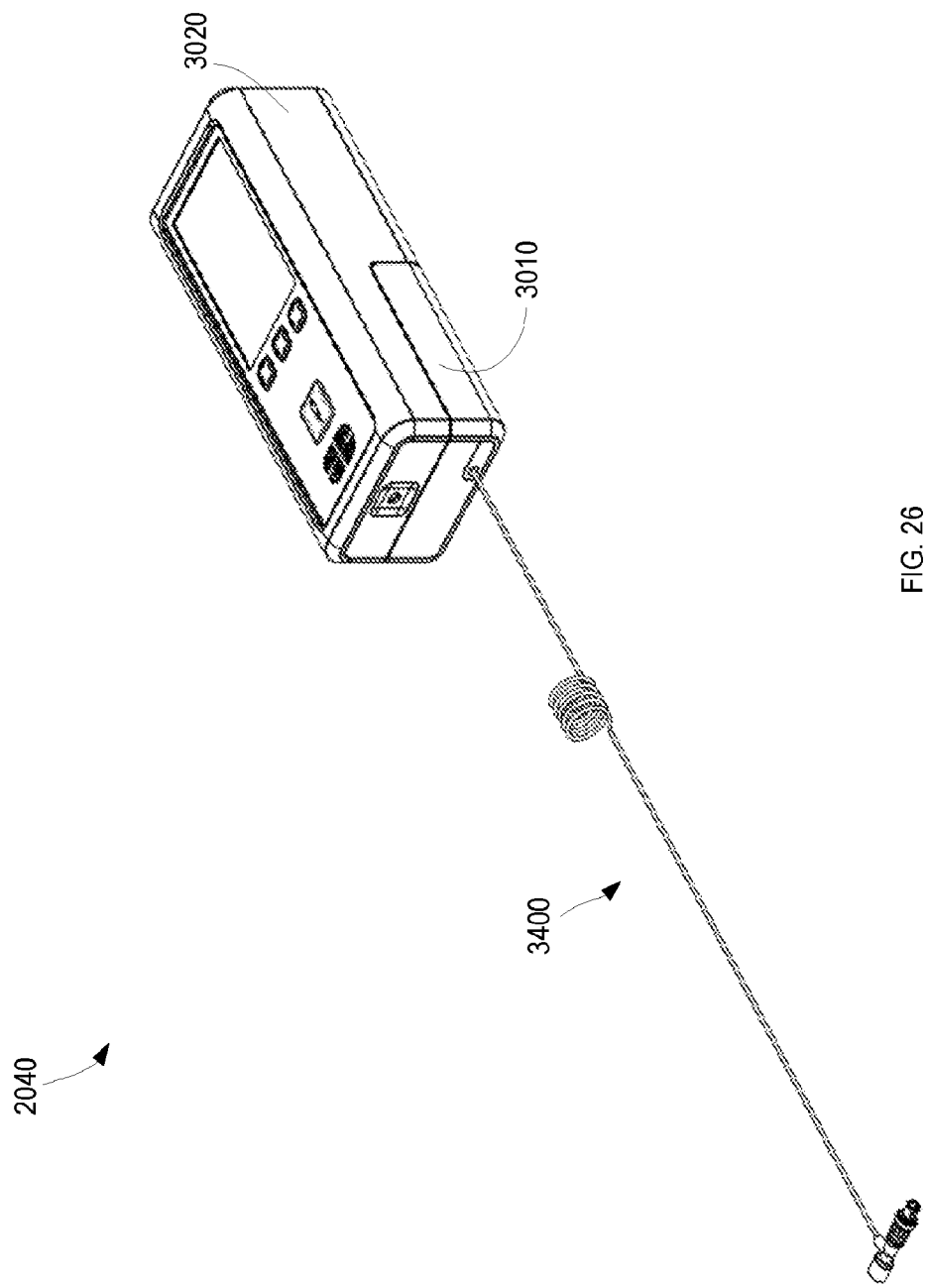
FIG. 26 is a perspective view of an acute medical condition response system in an assembled configuration according to an embodiment.

Referring to FIGS. 24-25B, the tube set 2400 includes a tube 2410 and a T-connector 2420. The tube 2410 has a proximal tube end 2412 and a distal tube end 2414. In some embodiments, the proximal tube end 2412 is fixedly coupled to the manifold housing 2310. For example, the proximal tube end 2412 can be affixed to the manifold housing 2310 in fluid communication with the receiving volume 2312 by any suitable coupling mechanism (e.g., via an adhesive, epoxy, plastic weld, or mechanical clamp intended to be permanent).

The T-connector 2420 of the tube set 2400 includes a central connector portion 2422 extending between a proximal connector end 2424 and a distal connector end 2426. The distal tube end 2414 is fixedly coupled to the central connector portion 2422. For example, in some embodiments, the distal tube end 2414 can be coupled to the central connector portion 2422 via an adhesive, rather than via a reversible coupling member (e.g., a Luer lock or other similar structure). However, in some embodiments, the distal tube end 2414 is removably coupled to the central connector portion 2422 (such as via a Luer lock). An IV check-valve 2430 is removably coupled at the distal connector end 2426. The IV check-valve 2430 can facilitate the coupling of the cartridge assembly 2010 to the medical port (e.g., a vascular access device). The proximal connector end 2424 includes an access port 2440 (e.g., an auxiliary port). The access port 2440 can facilitate the introduction of additional medicaments and/or fluids during the response to the acute medical condition without necessitating the decoupling of the cartridge assembly 2010 from the medical port. For example, in some embodiments, a secondary saline supply 2040 can be removably coupled to the access port 2440 of the T-connector 2420. The employment of the secondary saline supply 2040 can facilitate delivery of the medicament from the cartridge assembly 2010 by maintaining an open line (i.e., maintaining the patency of the medical port) during intervals between doses.

Each of the components of the cartridge assembly 2010 and the medical port through which the medicament is conveyed during delivery to a patient is characterized by a volume and a flow surface area, which can impact the accuracy and/or dose availability of the delivered medicament. Specifically, the delivery volume magnitude corresponds to the fluid volumes of the various components through which a dose of the medicament must traverse to be delivered to the patient. For example, the delivery volume magnitude includes the fluid volume of the receiving volume 2312, the fluid volume of the tube 2410, and the fluid volume of the medical port (as well as the fluid volume of any of the connectors between these components, including the puncturers, valves, etc.). The fluid volume of each of the components is affected by the physical dimensions of the component. In some embodiments, any of these components can be configured so that the delivery volume magnitude of the system is within a desired range to facilitate accurate dosing of medicament. For example, if the delivery volume magnitude is too high, then for a small dose volume the accuracy of dose delivery may be limited. Moreover, the amount of saline needed to flush the lines will increase, which can potentially cause the size of the cartridge to be increased to accommodate additional saline. Accordingly, in some embodiments, the tube has a ratio of a maximal length $L_M$ to an inner diameter ID of between 690:1 and 850:1, inclusive. Maximizing the length of the tube 2410 increases the usability of the system 2000 by facilitating the locating of the system 2000 in positions that maintain access to the pump assembly 2020 while not interfering with other treatment efforts. Accordingly, in order to maintain the desired fluid volume of the tube 2410, the inner diameter ID of the tube is decreased as the maximal length $L_M$ is increased. For example, the tube 2410 can have an inner diameter ID of 1.02 mm when the maximal length $L_M$ is 760 mm.

Referring again to FIG. 5A, the wall formed by the first wall piece 2110 and the second wall piece 2111 defines a maximal circumference $C_1$ of a cross-section that is perpendicular to the longitudinal axis $A_L$. The distal end portion 2119 of the wall defines a neck region 2160. The neck region 2160 has a cross-sectional circumference $C_2$ that is less than the maximal circumference $C_1$. Said another way, the neck region 2160 is concave relative to the proximal portion 2118 of the housing 2100. The neck region 2160 includes a set of grip enhancement features 2162. The grip enhancement features 2162 can include ridges, textures, bumps, depressions configured to facilitate handling of the cartridge assembly 2010 by an operator.

In some embodiments, a cartridge assembly can include one or more energy storage members or biasing members to facilitate actuation of the cartridge assembly after the cartridge assembly is coupled to a pump assembly. For example, FIGS. 26-33 depict various aspects of an acute medical condition response system (system) (also referred to as an Automated Medication Administration System (AMAS) or "system") 3000. As described herein, the system 3000 is configured to automate certain aspects of a response to an acute medical condition, such as cardiac arrest. Accordingly, the system 3000 utilizes a sealed cartridge assembly 3010 containing more than one dose of a drug (e.g., epinephrine, amiodarone hydrochloride, or other desired medicament) and more than one dose of a separate saline solution. The cartridge assembly 3010 is configured to be operably coupled between a pump assembly 3020 and a medical port (not shown) that is inserted into or attached to a patient. In this manner, the system 3000 can be used with a conventional medical port. The cartridge assembly 3010 includes a housing 3100 having a wall that defines an internal volume 3120 (see FIG. 30) and includes a coupling member 3130. The coupling member 3130 is positioned to engage a coupling interface 3650 of the pump assembly 3020. A set of cartridges 3200 is positioned within the internal volume 3120. The cartridges 3200 of the cartridge assembly 3010 are substantially similar to the cartridges 2200 described above. In this embodiment, the cartridge assembly 3010 includes a first cartridge 3210 that contains saline, a second cartridge 3230 that contains a first medicament, and a third cartridge 3250 that contains a second medicament. A manifold assembly 3300 is also positioned within the internal volume 3120. The manifold assembly 3300 includes a set of puncturers 3320 oriented to fluidically couple each of the cartridges 3200 to a tube set 3400 when the cartridge assembly 3010 is actuated. However, a gate member 3500 is also positioned within the internal volume 3120 to maintain a separation distance SD (see FIG. 32) between the set of puncturers 3320 and the set of cartridges 3200 when the cartridge assembly 3010 is in a storage configuration as depicted in FIG. 32. In this manner, the gate member 3500 functions as a safety to prevent the undesired or premature actuation of the cartridge assembly 3010.

Figure 29:
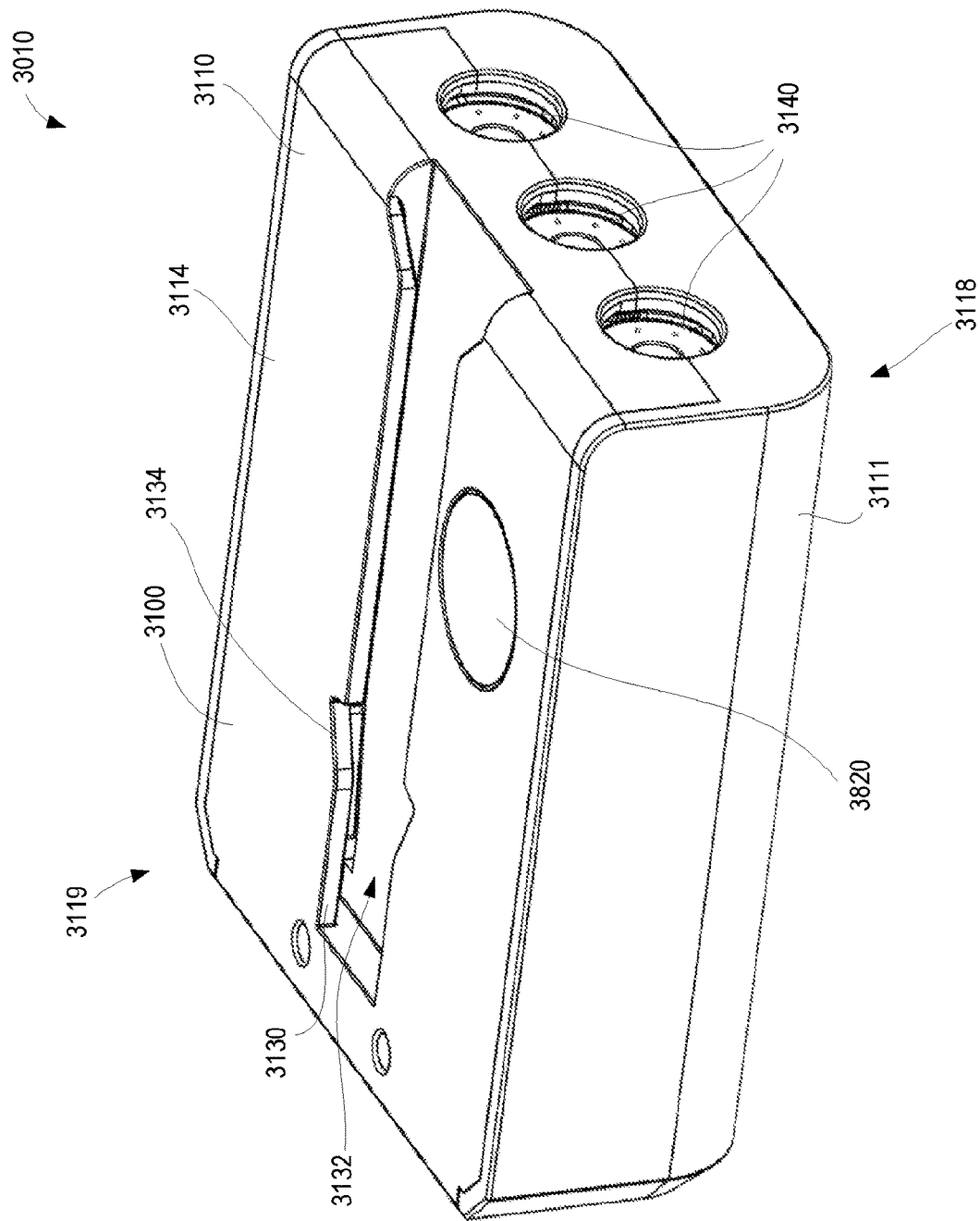
FIG. 29 is a perspective view of the cartridge assembly of the system of FIG. 26.

Referring to FIGS. 29 and 30, the cartridge assembly 3010 includes a first wall piece 3110 and a second wall piece 3111 that are coupled together to form a wall of the housing 3100. In some embodiments, the first wall piece 3110 is formed as an upper wall segment extending between a proximal portion 3118 and a distal end portion 3119 of the housing 3100. Similarly, the second wall piece 3111 can be formed as a lower wall segment extending between the proximal portion 3118 and the distal end portion 3119 of the housing 3100. The wall formed by the first wall piece 2110 and a second wall piece 2111 includes an inner face 3112. The inner face 3112 defines the internal volume 3120.

As depicted in FIG. 29 for example, an outer face 3114 of the wall (e.g., of the first wall piece 3110) includes the coupling member (or feature) 3130. The coupling feature 3130 includes a keyway 3132 and a receiver structure 3134. The keyway 3132 is configured to receive a mating coupling protrusion 3652 (FIG. 27) of the pump assembly 3020 configured as a T-track. The receiver structure 3134 is configured to receive a latch member 3660 of the pump assembly 3020. Further functions and features of the coupling feature 3130 are as described above with regards to the coupling feature 2130.

The first wall piece 3110 and the second wall piece 3111 are formed with multiple sets of cradles 3116. The cradles 3116 are sized and positioned to at least partially surround the plurality of cartridges 3200. As such, the plurality of cradles 3116 can align and secure the plurality of cartridges 3200 in a fixed longitudinal position. The set of cradles 3116 at the proximal end portion 3118 define a portion of a boundary of a set of access orifices 3140. Thus, when the first wall piece 3110 is coupled to the second wall piece 3111, the housing 3100 defines the set of access orifices 3140 that are aligned with the elastomeric members of each cartridge 3200. In this manner, in some embodiments, a drive member 3710 of the pump assembly 3020 can exert a force on the elastomeric member of each cartridge 3200 to cause delivery of the medicament therefrom. Additionally, the housing 3100 can be formed with a status opening 3117. The status opening can be utilized by a user of the cartridge assembly 3010 to verify the contents of the cartridge assembly 3010 before or after employment. In some embodiments, the housing 3100 can also define and/or support a sensor interface 3820 for engaging with a sensing element 3810 of the pump assembly 3020. The sensor interface 3820 can be as described above with reference to the sensor interface 2820.

Figure 31B:
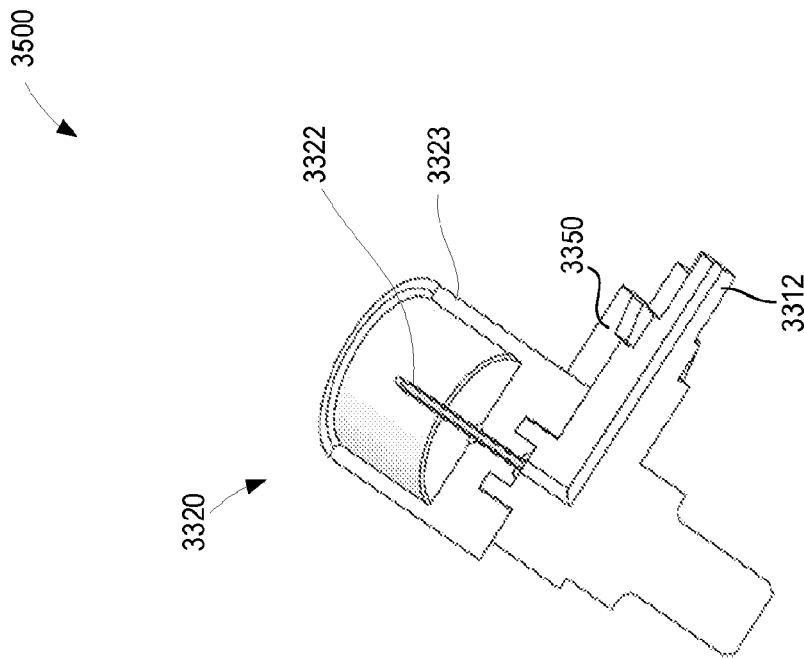
FIG. 31B is a cross-sectional view of the manifold segment of FIG. 31A taken at $Z_4$-$Z_4$.
Figure 31A:
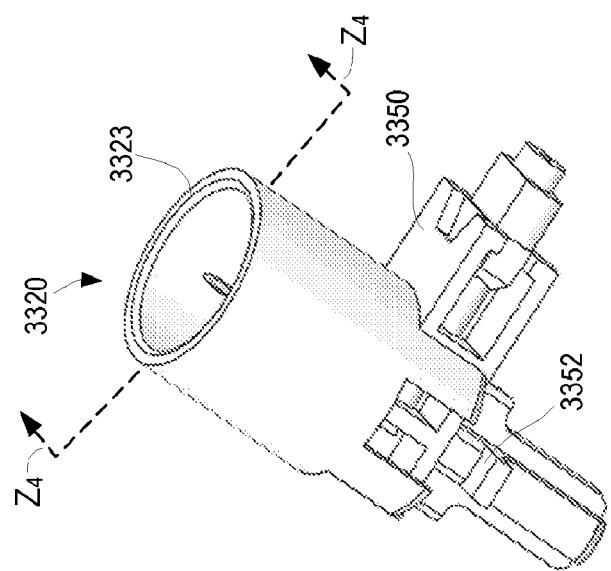
FIG. 31A is a perspective view of a manifold segment of a manifold assembly of the cartridge assembly according to an embodiment.

Referring to FIGS. 30-31B, manifold assembly 3300 includes a set of manifold segments 3350, a set of one-way valves (not shown) (see, e.g., the one-way valves 2330 described above) and a set of puncturers 3320. Each puncturer 3320 includes a needle 3322 circumscribed by a cylindrical housing 3323. Each puncturer 3320 is coupled to a manifold segment 3350, as depicted in FIGS. 31A and 31B. The one-way valves are positioned between each manifold segment 3350 and the puncturer 3320 coupled thereto. (The one-way valves may be formed and function as described above with reference to the one-way valves 2330.) The set of manifold segments 3350 are, as depicted in FIG. 30, intercoupled to form a manifold housing 3310. The manifold housing 3310 defines a receiving volume 3312, which is in fluid communication with the tube set 3400. The tube set 3400 is substantially similar to the tube set 2400 described above.

In some embodiments, at least one energy storage device 3360 (e.g., a spring or other biasing member) is positioned within the internal volume 3120 between the inner face 3112 of the wall and the manifold housing 3310. The energy storage device(s) 3360 is in contact with the manifold housing 3310. The energy storage device(s) 3360 is configured to exert a force on the manifold housing 3310. In response to the force and when the gate 3500 is moved, the manifold assembly 3300 moves in a proximal direction from a stored position Sp, as depicted in FIG. 32. Said another way, upon actuation of the cartridge assembly 3010, the manifold assembly 3300 moves in a proximal direction toward the cartridges 3200, which remain at a fixed longitudinal position relative to the housing 3100.

In some embodiments, the cartridge assembly 3010 is transitioned from a stored state $S_S$ (FIG. 32) to an actuated state $S_A$ (FIG. 33) via the coupling of the cartridge assembly 3010 to the pump assembly 3020. When the cartridge assembly 3010 is in the stored state $S_S$, the separation distance SD is maintained between the puncturers 3320 and the cartridges 3200 by the gate 3500. In other words, the proximal end of each of the needle 3322 is separated from a corresponding axially-aligned cartridge 3200 prior to the actuation of the cartridge assembly 3010. However, as depicted in FIG. 33, when the cartridge assembly 3010 is actuated, via the coupling to the pump assembly 3020, the plurality of cartridges 3200 are fluidically coupled to the receiving volume 3312 via the puncturers 3320.

Figure 33:
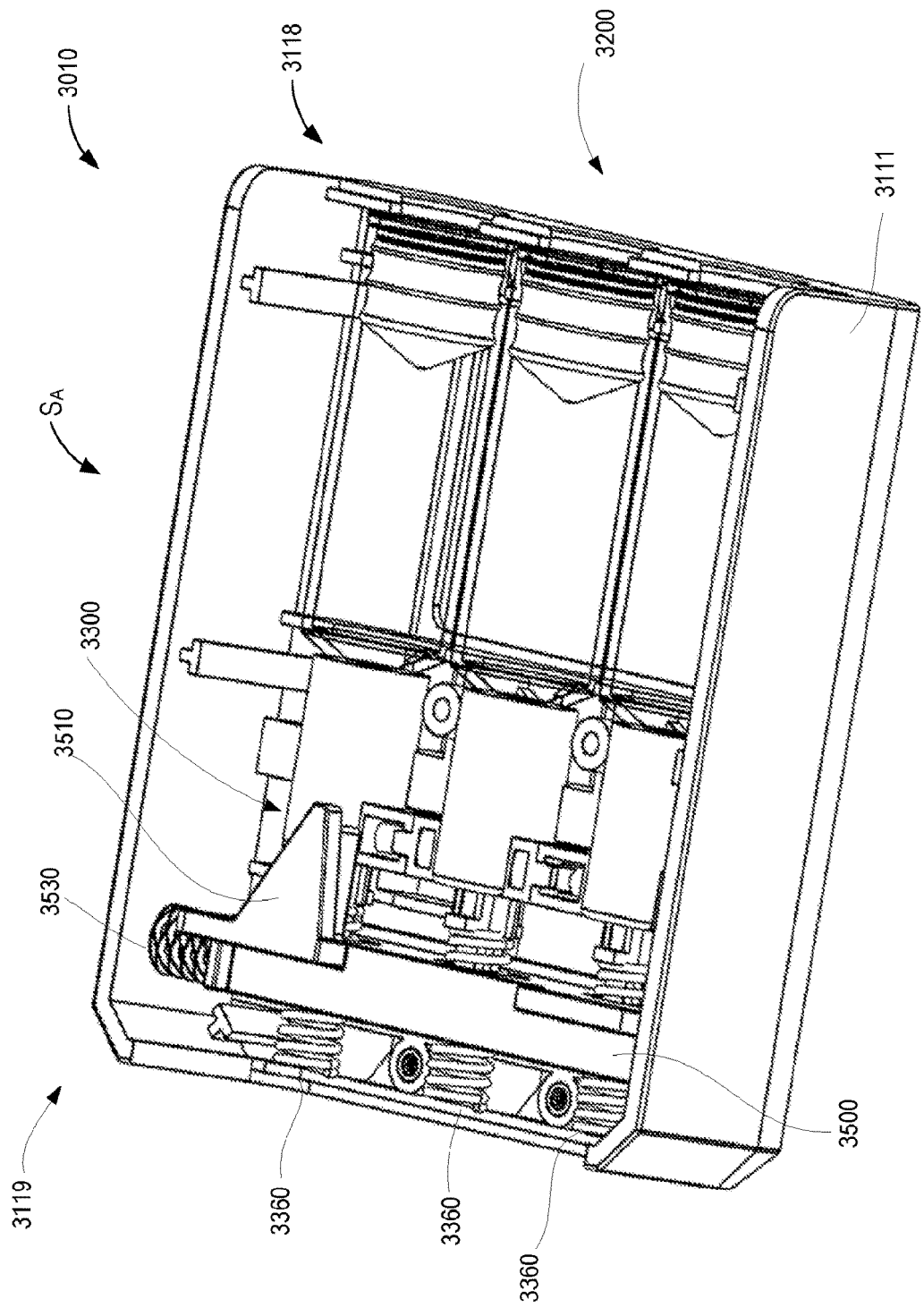
FIG. 33 is a perspective view of the cartridge assembly of FIG. 29 with a portion of the housing removed.

As depicted in FIGS. 32 and 33, the gate member 3500 is positioned within the internal volume 3120. When in a locked position $P_L$ (e.g., a locked orientation, an initial orientation, or a nominal position), the gate member 3500 maintains the separation distance SD between the puncturers 3320 and the cartridges 3200. The gate member 2500 is in the locked position $P_L$, as depicted in FIG. 32, when the cartridge assembly 3010 is in the stored state $S_S$.

In the lock position $P_L$, the gate member 3500 has an actuation portion 3510 that is at a position between the outer face 3114 and the coupling member. In other words, the actuation portion 3510 extends from the internal volume 3120 through the first wall piece 3110. The actuation portion 3510 is positioned such that when the cartridge assembly 3010 is coupled to the pump assembly 3020, the actuation portion 3510 is engaged by a protrusion 3652 of the coupling interface 3650 of the pump assembly 3020. The engagement of the actuation portion 3510 by the protrusion 3652 results in a lateral movement of the actuation portion 3510 and thus the gate member 3500. This lateral movement transitions the gate member 3500 from the locked position $P_L$, at least temporarily, to an unlocked position, and thereby, releases the manifold assembly 3300 to respond to the force exerted by the energy storage device(s) 3360.

The gate member 3500 includes an engagement member 3520. The engagement member 3520 is a substantially stiff structure that is oriented to engage at least one retaining ledge 3352 (FIG. 31A) of the manifold housing 3310 when in the locked position $P_L$. The engagement of the retaining ledge(s) 3352 by the engagement member 3520 maintains the manifold assembly 3300 in the stored position SP, as depicted in FIG. 32. The lateral movement of the actuation portion 3510 results in the engagement member 3520 disengaging from the retaining ledge(s) 3352. Accordingly, the gate member 3500 is disengaged from the retaining ledge(s) 3352 when in an unlocked position. The transition of the gate member to the unlock position corresponds to an actuation of the energy storage device(s) 3360 and a corresponding proximal movement of the manifold assembly 3300.

The gate member 3500 includes at least one spring element (or portion) 3530. The spring element(s) 3530 is positioned between the engagement member 3520 and the inner face 3112 of the wall. The spring element(s) 3530 biases the engagement member 3520 in (e.g., toward) the locked position $P_L$ when the cartridge assembly 3010 is in the stored state $S_S$. In other words, the spring element(s) 3530 exerts a force on the engagement member 3520 toward the locked position $P_L$ when the actuation portion 3510 is in a nominal position. Accordingly, when the actuation portion 3510 is engaged and the gate member 3500 transitions to the unlock position, the spring element(s) 3530 is compressed.

Any of the cartridge assemblies or cartridges shown and described herein can include any suitable medicament. For example, in some embodiments, a cartridge assembly (e.g., the cartridge assembly 2010 and 3010) can include one cartridge containing saline (e.g., 0.9%), one cartridge containing epinephrine and one cartridge containing amiodarone hydrochloride. In some embodiments, a cartridge assembly can include any suitable amount, concentration, and/or formulation of epinephrine, amiodarone hydrochloride, or saline. For example in some embodiments, any of the cartridge assemblies described herein can be configured for either an adult dosage or a pediatric dosage. Table 1 below provides one example of medicaments and saline that can be included in such configurations.

TABLE 1

| Cartridge | Cartridge contents | Adult Configuration | Pediatric Configuration |
|---|---|---|---|
| 1 | Epinephrine | 1.0 mg/mL, 12.0 mL | 0.1 mg/mL 12.0 mL |
| 2 | Amiodarone HCl | 50 mg/mL, 12.0 mL | 50 mg/mL, 12.0 mL |
| 3 | 0.9% Sodium Chloride | 9 mg/mL, 12.0 mL | 9 mg/mL, 12.0 mL |

In some embodiments, any of the cartridge assemblies or any of the cartridges can contain amiodarone hydrochloride having the formulation as indicated in Table 2.

TABLE 2

| | Product | Amiodarone Hydrochloride Injection USP, 50 mg/mL, Single patient use cartridge |
|---|---|---|
| Active Ingr. | Amiodarone Hydrochloride USP | 50 mg/mL (as the HCl) |
| Excipients | Sulfobutylether β-cyclodextrin | 225 mg/mL |
| | Citric Acid Monohydrate | 3.77 mg/ml |
| | Sodium Citrate Dihydrate | 2.10 mg/mL |
| | Sodium Hydroxide | qs to adjust pH |
| | Sodium Citrate Dihydrate | qs to adjust pH |
| Fill Volume | | 12.0 mL* |
| Dosage Form | | Injection (Solution) |
| Configuration | | 600 mg/12.0 mL* in clear glass cartridge |
| Route of Administration | | Intravenous (Bolus) |
| Strength | | 50 mg/mL |
| Strength Concentration for Administration to Patient | | 50 mg/mL |
| Indication | | Acute treatment of ventricular arrhythmias refractory to defibrillation, in adult and pediatric patients in cardiac arrest. |

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, although the cartridges contained within the cartridge assemblies are shown as being the same size and having the same features, in other embodiments, any of the cartridge assemblies described herein can have one cartridge that is of a different size than the other cartridges within the cartridge assembly. For example, in some embodiments, a cartridge assembly (e.g., the cartridge assembly 2010 or 3010) can include a first cartridge for containing saline that has a greater volume than the cartridges that contain medicaments to be delivered.

Although the cartridges assemblies are shown herein as having a cartridges containing medicaments therein, in other embodiments, a cartridge assembly can include one or more cartridges that are devoid of any medicament that can be used for training purposes. For example, in some embodiments a training cartridge assembly can include cartridges that have the color-coded crimp seals and a viewing window (as described herein), but can be devoid of any medicament. Such a training cartridge assembly can allow a user to practice coupling and decoupling a cartridge assembly to the pump assembly, as well as to simulate actual use (e.g., by actuating the pump assembly).

In some embodiments, a system can include one or more cartridge assembly blanks that are devoid of any cartridges. A cartridge assembly blank can have similar external features as any of the cartridge assemblies described herein (e.g., a coupling member similar to the coupling member 2130). The cartridge assembly blank can be coupled to the pump assembly to limit any damage to the drive portions of the pump assembly when the system is not in use.

Although various embodiments have been described as having particular features and/or combinations of components, other embodiments are possible having a combination of any features and/or components from any of embodiments as discussed above.

Further aspects of the invention are provided by the subject matter of the following clauses:

Clause 1. A cartridge assembly configured to be operatively coupled between a pump assembly and a medical port, the cartridge assembly comprising: a housing having a wall, an inner face of the wall defining an internal volume, an outer face of the wall having a coupling member positioned to engage a coupling interface of the pump assembly; a first cartridge positioned within the internal volume, the first cartridge including a first container body, a first frangible seal coupled to the first container body, and a first elastomeric member disposed within the first container body to retain a portion of saline within the first cartridge; a second cartridge positioned within the internal volume, the second cartridge including a second container body, a second frangible seal coupled to the second container body, and a second elastomeric member disposed within the second container body to retain a portion of a first medicament within the second cartridge; a manifold assembly positioned within the internal volume, the manifold assembly including: a manifold housing defining a receiving volume, a plurality of puncturers in fluid communication with the receiving volume and oriented to puncture the first frangible seal and the second frangible seal, and a plurality of one-way valves disposed between the plurality of puncturers and the receiving volume; a tube set coupled to the manifold assembly in fluid communication with the receiving volume, the tube set configured to be coupled to the medical port; and a gate member positioned within the internal volume and having an actuation portion at a position between the outer face and the coupling member, the gate member maintaining a separation distance between the plurality puncturers and the first frangible seal and the second frangible seal when in a locked position when the cartridge assembly is in a stored state.

Clause 2. The cartridge assembly of any preceding clause, wherein the first cartridge and the second cartridge are fluidically coupled to the receiving volume via the plurality of puncturers when the cartridge assembly is in an actuated state; and a coupling location of the first cartridge is upstream of a coupling location of the second cartridge.

Clause 3. The cartridge assembly of any preceding clause, further comprising a third cartridge positioned within the internal volume, the third cartridge including a third container body, a third frangible seal coupled to the third container body, and a third elastomeric member disposed within the third container body to retain a portion of a second medicament within the third cartridge, wherein: the second medicament is a different medicament from the first medicament, the first cartridge, the second cartridge, and the third cartridge are fluidically coupled to the receiving volume via the plurality of puncturers when the cartridge assembly is in an actuated state; and a coupling location of the first cartridge is upstream of a coupling location of the second cartridge and a coupling location of the third cartridge.

Clause 4. The cartridge assembly of any preceding clause, wherein the manifold assembly includes a manifold base coupled between the manifold housing and the first cartridge, the plurality puncturers are retained by the manifold base and include at least one bent needle having a plurality of bends; and the receiving volume has a sealed end portion and an outlet end portion joined by an input portion, the plurality of one-way valves are disposed along the input portion, the sealed end portion is upstream of the plurality of one-way valves, and the outlet end portion is operably coupled to the tube set.

Clause 5. The cartridge assembly of any preceding clause, wherein the at least one bent needle is a unitary structure having a distal portion that defines a first axis, a proximal portion that defines a second axis, and a middle portion coupled between the proximal portion and the distal portion, the first axis is parallel to and displaced from the second axis.

Clause 6. The cartridge assembly of any preceding clause, wherein the housing defines a longitudinal axis; the manifold assembly is at the same fixed longitudinal position when the cartridge assembly is in both the stored state and an actuated state; and the first cartridge and the second cartridge are moveable within the internal volume, the first cartridge and the second cartridge are at a first longitudinal position when the cartridge assembly is in the stored state and at a second longitudinal position that is distal of the first longitudinal position when the cartridge assembly is in the actuated state.

Clause 7. The cartridge assembly of any preceding clause, wherein the gate member further includes an engagement member positioned within the internal volume and oriented to engage the first cartridge and the second cartridge, the engagement member limits a movement of the first cartridge and the second cartridge from a first longitudinal position in a distal direction when in the locked position; at least one spring element positioned between the engagement member and the inner face, the at least one spring element biasing the engagement member in a locked position when the cartridge assembly is in the stored state; and wherein the actuation portion is coupled to the engagement member and extends from the engagement member to the position between the outer face and the coupling member.

Clause 8. The cartridge assembly of any preceding clause, wherein the gate member is a unitary structure.

Clause 9. The cartridge assembly of any preceding clause, wherein each puncturer of the plurality puncturers includes a needle circumscribed by a cylindrical housing and each puncturer is coupled to a manifold segment of a plurality of manifold segments; the one-way valves are positioned between each manifold segment and the puncturer coupled thereto; and the plurality of manifold segments are intercoupled to form the manifold housing.

Clause 10. The cartridge assembly of any preceding clause, further comprising at least one energy storage device positioned within the internal volume between the inner face of the wall and the manifold housing and in contact with the manifold housing, wherein the at least one energy storage device is oriented to exert a force on the manifold housing to move the manifold assembly in a proximal direction from a stored position when actuated.

Clause 11. The cartridge assembly of any preceding clause, wherein the gate member engages at least one retaining ledge of the manifold housing when in the locked position to maintain the manifold assembly in the stored position; the gate member is disengaged from the at least one retaining ledge when in an unlocked position; and a transition of the gate member to the unlocked position corresponds to an actuation of the at least one energy storage device.

Clause 12. The cartridge assembly of any preceding clause, wherein the coupling member is a keyway sized to receive a protrusion of the coupling interface.

Clause 13. The cartridge assembly of any preceding clause, wherein the coupling member includes a receiver structure configured to accept a latch member of the coupling interface.

Clause 14. The cartridge assembly of any preceding clause, wherein the actuation portion of the gate member is positioned within the keyway.

Clause 15. The cartridge assembly of any preceding clause, wherein the tube set includes a tube having a proximal tube end and a distal tube end, the proximal tube end is fixedly coupled to the manifold housing; and a T-connector having a central connector portion extending between a proximal connector end and a distal connector end, wherein: the distal tube end is fixedly coupled to the central connector portion, an IV check-valve is removably coupled at the distal connector end, and the proximal connector end includes an access port.

Clause 16. The cartridge assembly of any preceding clause, wherein the tube has a ratio of a maximal length to an inner diameter of between 690:1 and 850:1 inclusive.

Clause 17. The cartridge assembly of any preceding clause, further comprising a secondary saline supply removably coupled to the access port of the T-connector.

Clause 18. The cartridge assembly of any preceding clause, wherein a proximal end portion of the housing defines a plurality of access orifices, each of the access orifices being sized to receive a drive member of the pump assembly.

Clause 19. The cartridge assembly of any preceding clause, wherein the proximal end portion of the housing defines at least one actuation slot configured to receive at least one actuation member of the pump assembly; and the at least one actuation member is configured to transfer a force to the first container body and to the second container body to transition the first cartridge and the second cartridge from a first longitudinal position to a second longitudinal position that is distal of the first longitudinal position when the cartridge assembly is in an actuated state.

Clause 20. The cartridge assembly of any preceding clause, wherein the wall further defines a coil recess; and the tube set is contained within the coil recess when the cartridge assembly is in the stored state.

Clause 21. The cartridge assembly of any preceding clause, wherein the housing defines a longitudinal axis; the wall defines a maximal circumference of a cross-section that is perpendicular to the longitudinal axis; a distal end portion of the wall defines a neck region having a cross-sectional circumference that is less than the maximal circumference; and the neck region includes a plurality of grip enhancement features.

What is claimed is:

1. A cartridge assembly configured to be operatively coupled between a pump assembly and a medical port, the cartridge assembly comprising:
    a housing having a wall, an inner face of the wall defining an internal volume, an outer face of the wall having a coupling member positioned to engage a coupling interface of the pump assembly;
    a first cartridge positioned within the internal volume, the first cartridge including a first container body, a first frangible seal coupled to the first container body, and a first elastomeric member disposed within the first container body to retain a portion of saline within the first cartridge;
    a second cartridge positioned within the internal volume, the second cartridge including a second container body, a second frangible seal coupled to the second container body, and a second elastomeric member disposed within the second container body to retain a portion of a first medicament within the second cartridge;
    a manifold assembly positioned within the internal volume, the manifold assembly including:
        a manifold housing defining a receiving volume,
        a plurality of puncturers in fluid communication with the receiving volume and oriented to puncture the first frangible seal and the second frangible seal, and
        a plurality of one-way valves disposed between the plurality of puncturers and the receiving volume;
    a tube set coupled to the manifold assembly in fluid communication with the receiving volume, the tube set configured to be coupled to the medical port; and
    a gate member positioned within the internal volume and having an actuation portion at a position between the outer face and the coupling member, the gate member maintaining a separation distance between the plurality puncturers and the first frangible seal and the second frangible seal when in a locked position when the cartridge assembly is in a stored state.

2. The cartridge assembly of claim 1, wherein:
    the first cartridge and the second cartridge are fluidically coupled to the receiving volume via the plurality of puncturers when the cartridge assembly is in an actuated state; and
    a coupling location of the first cartridge is upstream of a coupling location of the second cartridge.

3. The cartridge assembly of claim 1, further comprising:
    a third cartridge positioned within the internal volume, the third cartridge including a third container body, a third frangible seal coupled to the third container body, and a third elastomeric member disposed within the third container body to retain a portion of a second medicament within the third cartridge, wherein:
the second medicament is a different medicament from the first medicament,
the first cartridge, the second cartridge, and the third cartridge are fluidically coupled to the receiving volume via the plurality of puncturers when the cartridge assembly is in an actuated state; and
a coupling location of the first cartridge is upstream of a coupling location of the second cartridge and a coupling location of the third cartridge.

4. The cartridge assembly of claim 1, wherein:
the manifold assembly includes a manifold base coupled between the manifold housing and the first cartridge;
the plurality of puncturers are retained by the manifold base and include at least one bent needle having a plurality of bends; and
the receiving volume has a sealed end portion and an outlet end portion joined by an input portion, the plurality of one-way valves are disposed along the input portion, the sealed end portion is upstream of the plurality of one-way valves, and the outlet end portion is operably coupled to the tube set.

5. The cartridge assembly of claim 4, wherein:
the at least one bent needle is a unitary structure having a distal portion that defines a first axis, a proximal portion that defines a second axis, and a middle portion coupled between the proximal portion and the distal portion, the first axis is parallel to and displaced from the second axis.

6. The cartridge assembly of claim 4, wherein:
the housing defines a longitudinal axis;
the manifold assembly is at the same fixed longitudinal position when the cartridge assembly is in both the stored state and an actuated state; and
the first cartridge and the second cartridge are moveable within the internal volume, the first cartridge and the second cartridge are at a first longitudinal position when the cartridge assembly is in the stored state and at a second longitudinal position that is distal of the first longitudinal position when the cartridge assembly is in the actuated state.

7. The cartridge assembly of claim 1, wherein the gate member further includes:
an engagement member positioned within the internal volume and oriented to engage the first cartridge and the second cartridge, the engagement member limits a movement of the first cartridge and the second cartridge from a first longitudinal position in a distal direction when in the locked position; and
at least one spring element positioned between the engagement member and the inner face, the at least one spring element biasing the engagement member in a locked position when the cartridge assembly is in the stored state,
wherein the actuation portion is coupled to the engagement member and extends from the engagement member to the position between the outer face and the coupling member.

8. The cartridge assembly of claim 7, wherein:
the gate member is a unitary structure.

9. The cartridge assembly of claim 1, wherein:
each puncturer of the plurality of puncturers includes a needle circumscribed by a cylindrical housing and each puncturer is coupled to a manifold segment of a plurality of manifold segments;
the one-way valves are positioned between each manifold segment and the puncturer coupled thereto; and
the plurality of manifold segments are intercoupled to form the manifold housing.

10. The cartridge assembly of claim 9, further comprising:
at least one energy storage device positioned within the internal volume between the inner face of the wall and the manifold housing and in contact with the manifold housing, wherein the at least one energy storage device is oriented to exert a force on the manifold housing to move the manifold assembly in a proximal direction from a stored position when actuated.

11. The cartridge assembly of claim 10, wherein:
the gate member engages at least one retaining ledge of the manifold housing when in the locked position to maintain the manifold assembly in the stored position;
the gate member is disengaged from the at least one retaining ledge when in an unlocked position; and
a transition of the gate member to the unlocked position corresponds to an actuation of the at least one energy storage device.

12. The cartridge assembly of claim 1, wherein:
the coupling member is a keyway sized to receive a protrusion of the coupling interface.

13. The cartridge assembly of claim 12, wherein:
the coupling member includes a receiver structure configured to accept a latch member of the coupling interface.

14. The cartridge assembly of claim 12, wherein:
the actuation portion of the gate member is positioned within the keyway.

15. The cartridge assembly of claim 1, wherein the tube set includes:
a tube having a proximal tube end and a distal tube end, the proximal tube end is fixedly coupled to the manifold housing; and
a T-connector having a central connector portion extending between a proximal connector end and a distal connector end, wherein:
the distal tube end is fixedly coupled to the central connector portion,
an IV check-valve is removably coupled at the distal connector end, and
the proximal connector end includes an access port.

16. The cartridge assembly of claim 15, wherein:
the tube has a ratio of a maximal length to an inner diameter of between 690:1 and 850:1 inclusive.

17. The cartridge assembly of claim 15, further comprising:
a secondary saline supply removably coupled to the access port of the T-connector.

18. The cartridge assembly of claim 1, wherein:
a proximal end portion of the housing defines a plurality of access orifices, each of the access orifices being sized to receive a drive member of the pump assembly.

19. The cartridge assembly of claim 18, wherein:
the proximal end portion of the housing defines at least one actuation slot configured to receive at least one actuation member of the pump assembly; and
the at least one actuation member is configured to transfer a force to the first container body and to the second container body to transition the first cartridge and the second cartridge from a first longitudinal position to a second longitudinal position that is distal of the first longitudinal position when the cartridge assembly is in an actuated state.

20. The cartridge assembly of claim 1, wherein:
the wall further defines a coil recess; and
the tube set is contained within the coil recess when the cartridge assembly is in the stored state.

21. The cartridge assembly of claim 1, wherein:
the housing defines a longitudinal axis;
the wall defines a maximal circumference of a cross-section that is perpendicular to the longitudinal axis;
a distal end portion of the wall defines a neck region having a cross-sectional circumference that is less than the maximal circumference; and
the neck region includes a plurality of grip enhancement features.

22. A cartridge assembly configured to be operatively coupled between a pump assembly and a medical port, the cartridge assembly comprising:
a housing having a wall, the wall defining an internal volume, an outer face of the wall having a coupling member positioned to engage a coupling interface of the pump assembly;
a cartridge positioned within the internal volume, the cartridge including a container body, a frangible seal coupled to the container body, and an elastomeric member disposed within the container body to retain a portion a medicament within the cartridge;
a manifold assembly positioned within the internal volume, the manifold assembly including a manifold housing defining a receiving volume and a puncturer in fluid communication with the receiving volume and oriented to puncture the frangible seal;
a tube set coupled to the manifold assembly in fluid communication with the receiving volume, the tube set configured to be coupled to the medical port; and
a gate member positioned within the internal volume and having an actuation portion at a position between the outer face and the coupling member, the gate member maintaining a separation distance between the puncturer and the frangible seal when in a locked position.

\* \* \* \* \*

UNITED STATES PATENT AND TRADEMARK OFFICE
CERTIFICATE OF CORRECTION

PATENT NO. : 12,121,695 B2
APPLICATION NO. : 18/687152
DATED : October 22, 2024
INVENTOR(S) : Eric S. Edwards et al.

Page 1 of 1

It is certified that error appears in the above-identified patent and that said Letters Patent is hereby corrected as shown below:

In the Claims

Column 24, Lines 52-53 - Claim 1, Lines 34-35 - "plurality puncturers" should be --plurality of punctures--

Signed and Sealed this
Fourteenth Day of January, 2025

Derrick Brent
*Acting Director of the United States Patent and Trademark Office*